United States Patent
Salzig et al.

(10) Patent No.: US 10,279,017 B2
(45) Date of Patent: May 7, 2019

(54) USE OF METALLOPROTEINASE INHIBITORS AGAINST BACTERIAL INFECTIONS

(71) Applicant: Fraunhofer-Gesellschaft zur Foederung der angewand Forschung e.V., Munich (DE)

(72) Inventors: Mark Salzig, Giessen (DE); Andreas Vilcinskas, Munich (DE); Rainer Fischer, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 15/322,838

(22) PCT Filed: Jul. 3, 2015

(86) PCT No.: PCT/EP2015/065210
§ 371 (c)(1),
(2) Date: Dec. 29, 2016

(87) PCT Pub. No.: WO2016/001410
PCT Pub. Date: Jan. 7, 2016

(65) Prior Publication Data
US 2017/0136107 A1 May 18, 2017

(30) Foreign Application Priority Data
Jul. 3, 2014 (EP) .................................. 14175566

(51) Int. Cl.
| | | |
|---|---|---|
| *A61L 2/16* | (2006.01) | |
| *A01N 43/16* | (2006.01) | |
| *A01N 63/02* | (2006.01) | |
| *A61K 38/57* | (2006.01) | |
| *A61K 45/06* | (2006.01) | |
| *A61K 48/00* | (2006.01) | |
| *C07K 14/81* | (2006.01) | |
| *A61K 31/7036* | (2006.01) | |

(52) U.S. Cl.
CPC .............. *A61K 38/57* (2013.01); *A01N 43/16* (2013.01); *A01N 63/02* (2013.01); *A61K 31/7036* (2013.01); *A61K 45/06* (2013.01); *A61L 2/16* (2013.01); *C07K 14/8146* (2013.01); *A61K 48/00* (2013.01); *A61L 2202/21* (2013.01)

(58) Field of Classification Search
CPC .... A01N 43/16; A01N 63/02; A61K 31/7036; A61K 38/57; A61K 48/00; A61L 2202/21; A61L 2/16; C07K 14/8146
See application file for complete search history.

(56) References Cited

PUBLICATIONS

Seitz et al. Identification of immunorelevant genes from greater wax moth (*Galleria mellonella*) by a subtractive hybridization approach. Developmental and Comparative Immunology, 2003. vol. 27, pp. 207-215. (Year: 2003).*
Hermann. Aminoglycoside antibiotics: old drugs and new therapeutic approaches. Cell. Mol. Life Sci. 2007, vol. 64, pp. 1841-1852. (Year: 2007).*
Cathcart et al. "Novel Inhibitors of the Pseudomonas aeroginosa Virulence Factor LasB: a Potential Therapeutic Approach for the Attenuation of Virulence Mechanisms in Pseudomonal Infection." Antimicrobial Agents and Chemotherapy, Jun. 2011, 55(6):2670-2678.
Caldwell et al. "Matrix metalloproteinase inhibitor within an absorbable coating for vascular applications: Delivery device characterization and the reduction of smooth muscle cell proliferation and migration." Journal of Biomedical Materials Research, Oct. 1, 2003, 67(1): 1-10.
Clermont et al. "Cloning and expression of an inhibitor of microbial metalloproteinases from insects contributing to innate immunity." The Biochemical Journal, Aug. 15, 2004, pp. 315-322.
Popov et al. "Effective antiprotease-antibiotic treatment of experimental anthrax." BMC Infectious Diseases, Apr. 8, 2005, 5(1):25, Biomed Central, London, GB.
Vilcinskas et al. "The greater wax moth *Galleria mellonella* as a mini-host model for human pathogens and as a reservoir of novel peptide antibiotics." Entomological Research, Aug. 2007, 37(Supp 1): p. A79.
Vilcinskas, Andreas. "Anti-infective Therapeutics from the Lepidopteran Model Host Galleria mellonella." Current Pharmaceutical Design, May 1, 2011, 17(13):1240-1245.
Wedde et al. "Purification and characterization of an inducible metalloprotease inhibitor from the hemolymph of greater wax moth larvae, *Galleria mellonella*." European Journal of Biochemistry, Aug. 1, 1998, 255(3):535-543, Wiley-Blackwell Publishing Ltd., GB.
PCT/EP2015/065210 International Search Report dated Sep. 21, 2015.

* cited by examiner

*Primary Examiner* — Marcela M Cordero Garcia
(74) *Attorney, Agent, or Firm* — Wagenknecht IP Law Group PC

(57) ABSTRACT

A composition comprising as components a polypeptide IMPIα (including wild type) and/or a polypeptide IMPIα-fusion and at least one antibiotic compound, in particular an aminoglycoside antibiotic, and/or at least one bactericidal compound, wherein the polypeptides, the at least one antibiotic and the at least one bactericidal compound is present in the composition in concentrations which exhibit in combination a synergistic effect against resistant bacteria.

Figure 1A:
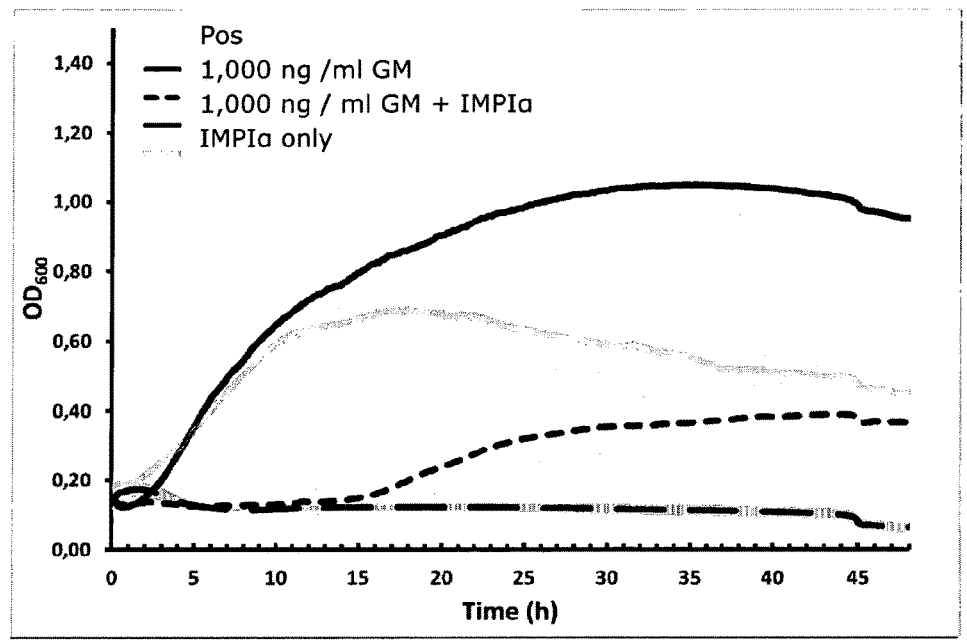
Figure 1B:
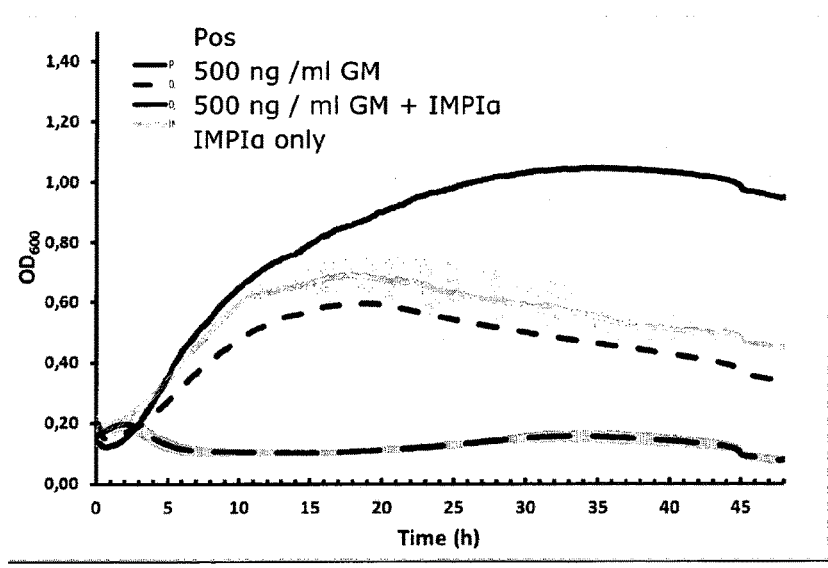
Figure 1C:
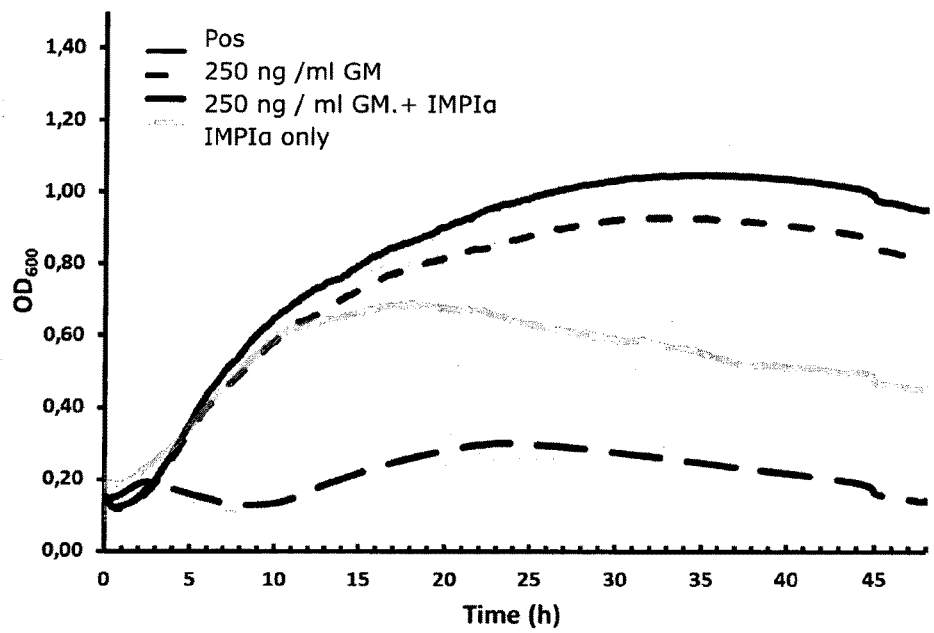
Figure 1D:
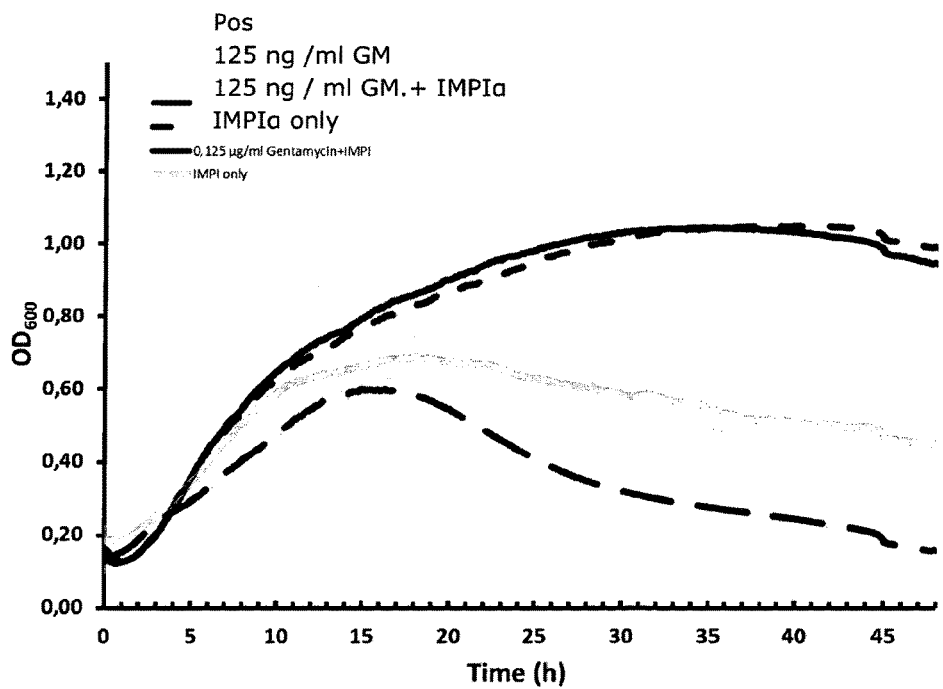

13 Claims, 17 Drawing Sheets
Specification includes a Sequence Listing.

Material examined: tracheal secretion
Diagnosis: V.a. infection

Examination for general bacteria (aerobic, anaerobic)
Examination for fungi

Culture result
K1 ++     *Pseudomonas aeruginosa*
           repetition isolation
K2 (+)    *Staphylococcus aureus*, test to follow
P1         *Candida albicans*
           *Candida albicans* is usually sensitive to amphotericin B;
           flucytosine, caspofungin, fluconazole, itraconazole,
           voriconazole and other imidazole preparations.
No detection of anaerobics.

Therapeutic comment
For *Pseudomonas* sp., fosfomycine should be employed only in combination therapies.

Hygiene instruction
Because of its resistance, the germ must be rated as a multi-resistant Gram-negative rod with resistance against 1 of 4 antibiotic classes (4MRGN). This requires isolation measures and optionally screening tests of contact patients (recommended by the RKI 10/2012). For details, see hygiene plan.

Comment
- The resistance test for bacteria is usually performed in accordance with the European standard EUCAST. Exceptions for which no evaluation criteria exist are tagged (§ or under the germ); in such a case, testing is performed in accordance with the American standard CLSI.

| Antibiogramm | K1 | K2 | | | |
|---|---|---|---|---|---|
| Gentamicin | R | | | | |
| Tobramycin | S | | | | |
| Penicillin G | | | | | |
| Oxacillin | | | | | |
| Piperacillin | R | | | | |
| Piperacillin/Tazobactam | R | | | | |
| Cefazolin | | | | | |
| Ceftazidim | R | | | | |
| Tetrazyklin | | | | | |
| Cotrimoxazol | | | | | |
| Erythromycin | | | | | |
| Clindamycin | | | | | |
| Levofloxacin | R | | | | |
| Ciprofloxacin | R | | | | |
| Vancomycin | | | | | |
| Meropenem | R | | | | |
| Cefepim | R | | | | |
| Fosfomycin § | S | | | | |
| Rifampicin | | | | | |
| Aztreonam | R | | | | |
| Colistin § | S | | | | |
| Amikacin | S | | | | |

Legend:   S=sensitive   I=intermediate   R=resistant
          P=positive    N=negative     MHK in µg/m

Figure 13

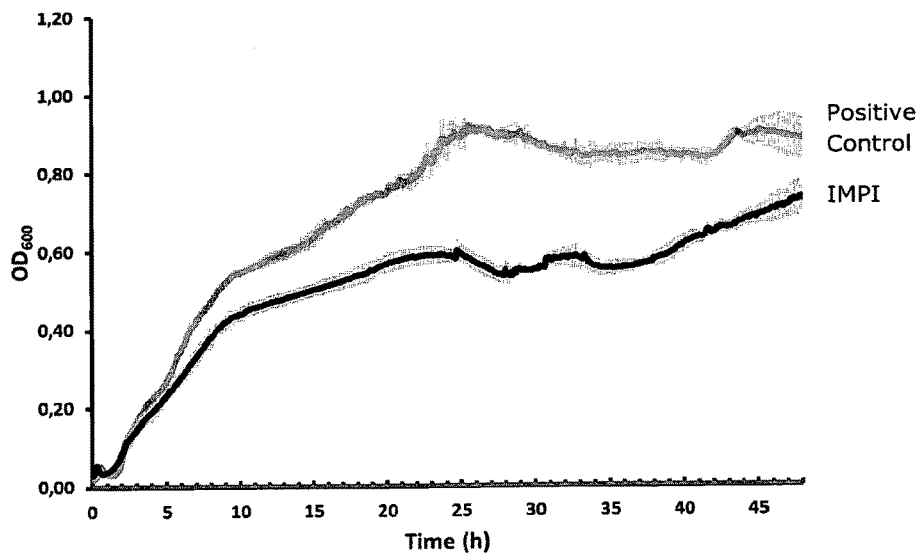

Figure 14a

SEQUENCE LISTING

```
<160> NUMBER OF SEQ ID NOS: 95

<210> SEQ ID NO 1
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 1 ata gtc cta att tgt aac ggt gga cac gaa tac tac gag tgc ggt gga    48
Ile Val Leu Ile Cys Asn Gly Gly His Glu Tyr Tyr Glu Cys Gly Gly
 1               5                  10                  15
```

```
gcc tgc gat aat gta tgt gca gat tta cat ata cag aat aaa aca aac         96
Ala Cys Asp Asn Val Cys Ala Asp Leu His Ile Gln Asn Lys Thr Asn
             20                  25                  30 tgt ccc atc att aat ata aga tgt aat gac aag tgc tac tgt gaa gat        144
Cys Pro Ile Ile Asn Ile Arg Cys Asn Asp Lys Cys Tyr Cys Glu Asp
         35                  40                  45 ggc tat gca agg gat gtc aat ggc aaa tgt ata ccg ata aaa gac tgt        192
Gly Tyr Ala Arg Asp Val Asn Gly Lys Cys Ile Pro Ile Lys Asp Cys
     50                  55                  60 cct aaa ata cgt tcg                                                    207
Pro Lys Ile Arg Ser
65

<210> SEQ ID NO 2
<211> LENGTH: 69
<212> TYPE: PRT
<213> ORGANISM: Galleria mellonella

<400> SEQUENCE: 2

Ile Val Leu Ile Cys Asn Gly Gly His Glu Tyr Tyr Glu Cys Gly Gly
 1               5                  10                  15

Ala Cys Asp Asn Val Cys Ala Asp Leu His Ile Gln Asn Lys Thr Asn
             20                  25                  30

Cys Pro Ile Ile Asn Ile Arg Cys Asn Asp Lys Cys Tyr Cys Glu Asp
         35                  40                  45

Gly Tyr Ala Arg Asp Val Asn Gly Lys Cys Ile Pro Ile Lys Asp Cys
     50                  55                  60

Pro Lys Ile Arg Ser
65

<210> SEQ ID NO 3
<211> LENGTH: 249
<212> TYPE: DNA
<213> ORGANISM: Galleria mellonella
<220> FEATURE:
<221> NAME/KEY: CDS
<222> LOCATION: (1)..(249)

<400> SEQUENCE: 3 cgt cgt tcc att ggg ata cca gtc gac aag aaa tgc tgc aca ggt cct         48
Arg Arg Ser Ile Gly Ile Pro Val Asp Lys Lys Cys Cys Thr Gly Pro
 1               5                  10                  15 aac gaa cac tat gac gaa gag aaa gta agc tgt cct cca gaa acc tgt         96
Asn Glu His Tyr Asp Glu Glu Lys Val Ser Cys Pro Pro Glu Thr Cys
             20                  25                  30 atc tcc ctt gtg gct aag ttt tcc tgc att gac tcc cct cca ccg tcg        144
Ile Ser Leu Val Ala Lys Phe Ser Cys Ile Asp Ser Pro Pro Pro Ser
         35                  40                  45 cca ggg tgt tct tgc aat tca gga tac tta aga ctt aac cta act tca        192
Pro Gly Cys Ser Cys Asn Ser Gly Tyr Leu Arg Leu Asn Leu Thr Ser
     50                  55                  60 cca tgc ata cca att tgc gat tgt cca caa atg caa cat tcc cct gat        240
Pro Cys Ile Pro Ile Cys Asp Cys Pro Gln Met Gln His Ser Pro Asp
65                  70                  75                  80 tgt caa taa                                                            249
Cys Gln <210> SEQ ID NO 4
<211> LENGTH: 82
<212> TYPE: PRT
<213> ORGANISM: Galleria mellonella
```

<400> SEQUENCE: 4

```
Arg Arg Ser Ile Gly Ile Pro Val Asp Lys Lys Cys Cys Thr Gly Pro
1               5                   10                  15

Asn Glu His Tyr Asp Glu Glu Lys Val Ser Cys Pro Pro Glu Thr Cys
            20                  25                  30

Ile Ser Leu Val Ala Lys Phe Ser Cys Ile Asp Ser Pro Pro Ser
        35                  40                  45

Pro Gly Cys Ser Cys Asn Ser Gly Tyr Leu Arg Leu Asn Leu Thr Ser
    50                  55                  60

Pro Cys Ile Pro Ile Cys Asp Cys Pro Gln Met Gln His Ser Pro Asp
65                  70                  75                  80

Cys Gln
```

<210> SEQ ID NO 5
<211> LENGTH: 1041
<212> TYPE: DNA
<213> ORGANISM: Galleria mellonella
<220> FEATURE:
<221> NAME/KEY: CDS
<222> LOCATION: (1)..(1041)

<400> SEQUENCE: 5

```
atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
            85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
        100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
    115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
            165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
        180                 185                 190 ttg aaa tcc agc aag tat ata gca tgg cct ttg cag ggc tgg caa gcc     624
```

```
Leu Lys Ser Ser Lys Tyr Ile Ala Trp Pro Leu Gln Gly Trp Gln Ala
            195                 200                 205 acg ttt ggt ggc ggc gac cat cct cca aaa tcg gat ggt tca act agt      672
Thr Phe Gly Gly Gly Asp His Pro Pro Lys Ser Asp Gly Ser Thr Ser
210                 215                 220 ggt tct ggt cat cac cat cac cat cac tcc gcg ggt ctg gtg cca cgc      720
Gly Ser Gly His His His His His His Ser Ala Gly Leu Val Pro Arg
225                 230                 235                 240 ggt agt act gca att ggt atg aaa gaa acc gct gct gct aaa ttc gaa      768
Gly Ser Thr Ala Ile Gly Met Lys Glu Thr Ala Ala Ala Lys Phe Glu
            245                 250                 255 cgc cag cac atg gac agc cca gat ctg ggt acc ggt ggt ggc tcc ggt      816
Arg Gln His Met Asp Ser Pro Asp Leu Gly Thr Gly Gly Gly Ser Gly
        260                 265                 270 gat gac gac gac aag ata gtc cta att tgt aac ggt gga cac gaa tac      864
Asp Asp Asp Asp Lys Ile Val Leu Ile Cys Asn Gly Gly His Glu Tyr
        275                 280                 285 tac gag tgc ggt gga gcc tgc gat aat gta tgt gca gat tta cat ata      912
Tyr Glu Cys Gly Gly Ala Cys Asp Asn Val Cys Ala Asp Leu His Ile
290                 295                 300 cag aat aaa aca aac tgt ccc atc att aat ata aga tgt aat gac aag      960
Gln Asn Lys Thr Asn Cys Pro Ile Ile Asn Ile Arg Cys Asn Asp Lys
305                 310                 315                 320 tgc tac tgt gaa gat ggc tat gca agg gat gtc aat ggc aaa tgt ata     1008
Cys Tyr Cys Glu Asp Gly Tyr Ala Arg Asp Val Asn Gly Lys Cys Ile
            325                 330                 335 ccg ata aaa gac tgt cct aaa ata cgt tcg tag                         1041
Pro Ile Lys Asp Cys Pro Lys Ile Arg Ser
        340                 345

<210> SEQ ID NO 6
<211> LENGTH: 346
<212> TYPE: PRT
<213> ORGANISM: Galleria mellonella

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
            260                 265                 270

Asp Asp Asp Asp Lys Ile Val Leu Ile Cys Asn Gly Gly His Glu Tyr
            275                 280                 285

Tyr Glu Cys Gly Gly Ala Cys Asp Asn Val Cys Ala Asp Leu His Ile
    290                 295                 300

Gln Asn Lys Thr Asn Cys Pro Ile Ile Asn Ile Arg Cys Asn Asp Lys
305                 310                 315                 320

Cys Tyr Cys Glu Asp Gly Tyr Ala Arg Asp Val Asn Gly Lys Cys Ile
                325                 330                 335

Pro Ile Lys Asp Cys Pro Lys Ile Arg Ser
            340                 345

<210> SEQ ID NO 7
<211> LENGTH: 1080
<212> TYPE: DNA
<213> ORGANISM: Galleria mellonella
<220> FEATURE:
<221> NAME/KEY: CDS
<222> LOCATION: (1)..(1080)

<400> SEQUENCE: 7 atg tcc cct ata cta ggt tat tgg aaa att aag ggc ctt gtg caa ccc       48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg       96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg      144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa      192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac      240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa      288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt      336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa      384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat      432
Met Leu Lys Met Phe Glu Asp Arg Leu Cys His Lys Thr Tyr Leu Asn
```

-continued

```
              130                 135                 140
ggt gat cat gta acc cat cct gac ttc atg ttg tat gac gct ctt gat    480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta    528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac    576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc    624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt    672
Thr Phe Gly Gly Gly Asp His Pro Pro Lys Ser Asp Gly Ser Thr Ser
    210                 215                 220 ggt tct ggt cat cac cat cac cat cac tcc gcg ggt ctg gtg cca cgc    720
Gly Ser Gly His His His His His His Ser Ala Gly Leu Val Pro Arg
225                 230                 235                 240 ggt agt act gca att ggt atg aaa gaa acc gct gct gct aaa ttc gaa    768
Gly Ser Thr Ala Ile Gly Met Lys Glu Thr Ala Ala Ala Lys Phe Glu
                245                 250                 255 cgc cag cac atg gac agc cca gat ctg ggt acc ggt ggt ggc tcc ggt    816
Arg Gln His Met Asp Ser Pro Asp Leu Gly Thr Gly Gly Gly Ser Gly
            260                 265                 270 gat gac gac gac aag cgt cgt tcc att ggg ata cca gtc gac aag aaa    864
Asp Asp Asp Asp Lys Arg Arg Ser Ile Gly Ile Pro Val Asp Lys Lys
        275                 280                 285 tgc tgc aca ggt cct aac gaa cac tat gac gaa gag aaa gta agc tgt    912
Cys Cys Thr Gly Pro Asn Glu His Tyr Asp Glu Glu Lys Val Ser Cys
    290                 295                 300 cct cca gaa acc tgt atc tcc ctt gtg gct aag ttt tcc tgc att gac    960
Pro Pro Glu Thr Cys Ile Ser Leu Val Ala Lys Phe Ser Cys Ile Asp
305                 310                 315                 320 tcc cct cca ccg tcg cca ggg tgt tct tgc aat tca gga tac tta aga    1008
Ser Pro Pro Pro Ser Pro Gly Cys Ser Cys Asn Ser Gly Tyr Leu Arg
                325                 330                 335 ctt aac cta act tca cca tgc ata cca att tgc gat tgt cca caa atg    1056
Leu Asn Leu Thr Ser Pro Cys Ile Pro Ile Cys Asp Cys Pro Gln Met
            340                 345                 350 caa cat tcc cct gat tgt caa tag                                    1080
Gln His Ser Pro Asp Cys Gln
        355
```

<210> SEQ ID NO 8
<211> LENGTH: 359
<212> TYPE: PRT
<213> ORGANISM: Galleria mellonella

<400> SEQUENCE: 8

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

-continued

```
                65                  70                  75                  80
        Met Leu Gly Gly Cys Pro Lys Glu Arg Ala Glu Ile Ser Met Leu Glu
                        85                  90                  95

Gly Ala Val Leu Asp Ile Arg Tyr Gly Val Ser Arg Ile Ala Tyr Ser
                        100                 105                 110

Lys Asp Phe Glu Thr Leu Lys Val Asp Phe Leu Ser Lys Leu Pro Glu
                        115                 120                 125

Met Leu Lys Met Phe Glu Asp Arg Leu Cys His Lys Thr Tyr Leu Asn
                    130                 135                 140

Gly Asp His Val Thr His Pro Asp Phe Met Leu Tyr Asp Ala Leu Asp
        145                 150                 155                 160

Val Val Leu Tyr Met Asp Pro Met Cys Leu Asp Ala Phe Pro Lys Leu
                        165                 170                 175

Val Cys Phe Lys Lys Arg Ile Glu Ala Ile Pro Gln Ile Asp Lys Tyr
                    180                 185                 190

Leu Lys Ser Ser Lys Tyr Ile Ala Trp Pro Leu Gln Gly Trp Gln Ala
                        195                 200                 205

Thr Phe Gly Gly Gly Asp His Pro Pro Lys Ser Asp Gly Ser Thr Ser
                    210                 215                 220

Gly Ser Gly His His His His His Ser Ala Gly Leu Val Pro Arg
        225                 230                 235                 240

Gly Ser Thr Ala Ile Gly Met Lys Glu Thr Ala Ala Lys Phe Glu
                        245                 250                 255

Arg Gln His Met Asp Ser Pro Asp Leu Gly Thr Gly Gly Ser Gly
                    260                 265                 270

Asp Asp Asp Asp Lys Arg Arg Ser Ile Gly Ile Pro Val Asp Lys Lys
                        275                 280                 285

Cys Cys Thr Gly Pro Asn Glu His Tyr Asp Glu Lys Val Ser Cys
                    290                 295                 300

Pro Pro Glu Thr Cys Ile Ser Leu Val Ala Lys Phe Ser Cys Ile Asp
        305                 310                 315                 320

Ser Pro Pro Ser Pro Gly Cys Ser Cys Asn Ser Gly Tyr Leu Arg
                        325                 330                 335

Leu Asn Leu Thr Ser Pro Cys Ile Pro Ile Cys Asp Cys Pro Gln Met
                    340                 345                 350

Gln His Ser Pro Asp Cys Gln
                355
```

<210> SEQ ID NO 9
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 9

```
ata gtc cta att tgt aac ggt gga cac gaa tac tac gag tgc ggt gga       48
Ile Val Leu Ile Cys Asn Gly Gly His Glu Tyr Tyr Glu Cys Gly Gly
1                5                  10                  15 gcc tgc gat aat gta tgt gca gat tta cat ata cag aat aaa aca aac       96
Ala Cys Asp Asn Val Cys Ala Asp Leu His Ile Gln Asn Lys Thr Asn
                20                  25                  30 tgt ccc atc att ggt ctg gct tgt aat gac aag tgc tac tgt gaa gat      144
Cys Pro Ile Ile Gly Leu Ala Cys Asn Asp Lys Cys Tyr Cys Glu Asp
            35                  40                  45
```

```
ggc tat gca agg gat gtc aat ggc aaa tgt ata ccg ata aaa gac tgt         192
Gly Tyr Ala Arg Asp Val Asn Gly Lys Cys Ile Pro Ile Lys Asp Cys
     50                  55                  60 cct aaa ata cgt tcg                                                      207
Pro Lys Ile Arg Ser
65

<210> SEQ ID NO 10
<211> LENGTH: 69
<212> TYPE: PRT
<213> ORGANISM: Galleria mellonella

<400> SEQUENCE: 10

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
                20                  25                  30

Cys Pro Ile Ile Gly Leu Ala Cys Asn Asp Lys Cys Tyr Cys Glu Asp
            35                  40                  45

Gly Tyr Ala Arg Asp Val Asn Gly Lys Cys Ile Pro Ile Lys Asp Cys
     50                  55                  60

Pro Lys Ile Arg Ser
65

<210> SEQ ID NO 11
<211> LENGTH: 1041
<212> TYPE: DNA
<213> ORGANISM: Galleria mellonella
<220> FEATURE:
<221> NAME/KEY: CDS
<222> LOCATION: (1)..(1041)

<400> SEQUENCE: 11 atg tcc cct ata cta ggt tat tgg aaa att aag ggc ctt gtg caa ccc          48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg          96
Thr Arg Leu Leu Leu Glu Tyr Leu Glu Glu Lys Tyr Glu Glu His Leu
                20                  25                  30 tat gag cgc gat gaa ggt gat aaa tgg cga aac aaa aag ttt gaa ttg         144
Tyr Glu Arg Asp Glu Gly Asp Lys Trp Arg Asn Lys Lys Phe Glu Leu
            35                  40                  45 ggt ttg gag ttt ccc aat ctt cct tat tat att gat ggt gat gtt aaa         192
Gly Leu Glu Phe Pro Asn Leu Pro Tyr Tyr Ile Asp Gly Asp Val Lys
     50                  55                  60 tta aca cag tct atg gcc atc ata cgt tat ata gct gac aag cac aac         240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa         288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt         336
Gly Ala Val Leu Asp Ile Arg Tyr Gly Val Ser Arg Ile Ala Tyr Ser
                100                 105                 110 aaa gac ttt gaa act ctc aaa gtt gat ttt ctt agc aag cta cct gaa         384
Lys Asp Phe Glu Thr Leu Lys Val Asp Phe Leu Ser Lys Leu Pro Glu
            115                 120                 125 atg ctg aaa atg ttc gaa gat cgt tta tgt cat aaa aca tat tta aat         432
Met Leu Lys Met Phe Glu Asp Arg Leu Cys His Lys Thr Tyr Leu Asn
     130                 135                 140 ggt gat cat gta acc cat cct gac ttc atg ttg tat gac gct ctt gat         480
```

```
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta         528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac         576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc         624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt         672
Thr Phe Gly Gly Gly Asp His Pro Pro Lys Ser Asp Gly Ser Thr Ser
    210                 215                 220 ggt tct ggt cat cac cat cac cat cac tcc gcg ggt ctg gtg cca cgc         720
Gly Ser Gly His His His His His His Ser Ala Gly Leu Val Pro Arg
225                 230                 235                 240 ggt agt act gca att ggt atg aaa gaa acc gct gct gct aaa ttc gaa         768
Gly Ser Thr Ala Ile Gly Met Lys Glu Thr Ala Ala Ala Lys Phe Glu
                245                 250                 255 cgc cag cac atg gac agc cca gat ctg ggt acc ggt ggt ggc tcc ggt         816
Arg Gln His Met Asp Ser Pro Asp Leu Gly Thr Gly Gly Gly Ser Gly
            260                 265                 270 gat gac gac gac aag ata gtc cta att tgt aac ggt gga cac gaa tac         864
Asp Asp Asp Asp Lys Ile Val Leu Ile Cys Asn Gly Gly His Glu Tyr
        275                 280                 285 tac gag tgc ggt gga gcc tgc gat aat gta tgt gca gat tta cat ata         912
Tyr Glu Cys Gly Gly Ala Cys Asp Asn Val Cys Ala Asp Leu His Ile
    290                 295                 300 cag aat aaa aca aac tgt ccc atc att ggt ctg gct tgt aat gac aag         960
Gln Asn Lys Thr Asn Cys Pro Ile Ile Gly Leu Ala Cys Asn Asp Lys
305                 310                 315                 320 tgc tac tgt gaa gat ggc tat gca agg gat gtc aat ggc aaa tgt ata        1008
Cys Tyr Cys Glu Asp Gly Tyr Ala Arg Asp Val Asn Gly Lys Cys Ile
                325                 330                 335 ccg ata aaa gac tgt cct aaa ata cgt tcg tag                            1041
Pro Ile Lys Asp Cys Pro Lys Ile Arg Ser
            340                 345

<210> SEQ ID NO 12
<211> LENGTH: 346
<212> TYPE: PRT
<213> ORGANISM: Galleria mellonella

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110
```

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Lys Phe Glu
                245                 250                 255

Arg Gln His Met Asp Ser Pro Asp Leu Gly Thr Gly Gly Ser Gly
            260                 265                 270

Asp Asp Asp Lys Ile Val Leu Ile Cys Asn Gly Gly His Glu Tyr
            275                 280                 285

Tyr Glu Cys Gly Gly Ala Cys Asp Asn Val Cys Ala Asp Leu His Ile
    290                 295                 300

Gln Asn Lys Thr Asn Cys Pro Ile Ile Gly Leu Ala Cys Asn Asp Lys
305                 310                 315                 320

Cys Tyr Cys Glu Asp Gly Tyr Ala Arg Asp Val Asn Gly Lys Cys Ile
                325                 330                 335

Pro Ile Lys Asp Cys Pro Lys Ile Arg Ser
            340                 345

<210> SEQ ID NO 13
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 13 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc atc att aat ata aga tgt aat gac aag tgc tac tgt gaa gat     144
Cys Pro Ile Ile Asn Ile Arg Cys Asn Asp Lys Cys Tyr Cys Glu Asp
        35                  40                  45 ggc tat gca aag gat gtc aat ggc aaa tgt ata ccg ata aaa gac tgt     192
Gly Tyr Ala Lys Asp Val Asn Gly Lys Cys Ile Pro Ile Lys Asp Cys
    50                  55                  60 cct aaa ata cgt tcg                                                  207
Pro Lys Ile Arg Ser
65

<210> SEQ ID NO 14

<211> LENGTH: 69
<212> TYPE: PRT
<213> ORGANISM: Galleria mellonella

<400> SEQUENCE: 14

```
Ile Val Leu Ile Cys Asn Gly Gly His Glu Tyr Tyr Glu Cys Gly Gly
1               5                   10                  15
Ala Cys Asp Asn Val Cys Ala Asp Leu His Ile Gln Asn Lys Thr Asn
            20                  25                  30
Cys Pro Ile Ile Asn Ile Arg Cys Asn Asp Lys Cys Tyr Cys Glu Asp
        35                  40                  45
Gly Tyr Ala Lys Asp Val Asn Gly Lys Cys Ile Pro Ile Lys Asp Cys
    50                  55                  60
Pro Lys Ile Arg Ser
65
```

<210> SEQ ID NO 15
<211> LENGTH: 1041
<212> TYPE: DNA
<213> ORGANISM: Galleria mellonella
<220> FEATURE:
<221> NAME/KEY: CDS
<222> LOCATION: (1)..(1041)

<400> SEQUENCE: 15

```
atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
            180                 185                 190
```

```
ttg aaa tcc agc aag tat ata gca tgg cct ttg cag ggc tgg caa gcc    624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt    672
Thr Phe Gly Gly Gly Asp His Pro Pro Lys Ser Asp Gly Ser Thr Ser
210                 215                 220 ggt tct ggt cat cac cat cac cat cac tcc gcg ggt ctg gtg cca cgc    720
Gly Ser Gly His His His His His His Ser Ala Gly Leu Val Pro Arg
225                 230                 235                 240 ggt agt act gca att ggt atg aaa gaa acc gct gct gct aaa ttc gaa    768
Gly Ser Thr Ala Ile Gly Met Lys Glu Thr Ala Ala Ala Lys Phe Glu
            245                 250                 255 cgc cag cac atg gac agc cca gat ctg ggt acc ggt ggc tcc ggt        816
Arg Gln His Met Asp Ser Pro Asp Leu Gly Thr Gly Gly Ser Gly
        260                 265                 270 gat gac gac gac aag ata gtc cta att tgt aac ggt gga cac gaa tac    864
Asp Asp Asp Asp Lys Ile Val Leu Ile Cys Asn Gly Gly His Glu Tyr
                275                 280                 285 tac gag tgc ggt gga gcc tgc gat aat gta tgt gca gat tta cat ata    912
Tyr Glu Cys Gly Gly Ala Cys Asp Asn Val Cys Ala Asp Leu His Ile
290                 295                 300 cag aat aaa aca aac tgt ccc atc att aat ata aga tgt aat gac aag    960
Gln Asn Lys Thr Asn Cys Pro Ile Ile Asn Ile Arg Cys Asn Asp Lys
305                 310                 315                 320 tgc tac tgt gaa gat ggc tat gca aag gat gtc aat ggc aaa tgt ata   1008
Cys Tyr Cys Glu Asp Gly Tyr Ala Lys Asp Val Asn Gly Lys Cys Ile
                325                 330                 335 ccg ata aaa gac tgt cct aaa ata cgt tcg tag                        1041
Pro Ile Lys Asp Cys Pro Lys Ile Arg Ser
            340                 345

<210> SEQ ID NO 16
<211> LENGTH: 346
<212> TYPE: PRT
<213> ORGANISM: Galleria mellonella

<400> SEQUENCE: 16

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160
```

```
Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
        180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
        210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Lys Phe Glu
                245                 250                 255

Arg Gln His Met Asp Ser Pro Asp Leu Gly Thr Gly Gly Ser Gly
            260                 265                 270

Asp Asp Asp Asp Lys Ile Val Leu Ile Cys Asn Gly Gly His Glu Tyr
        275                 280                 285

Tyr Glu Cys Gly Gly Ala Cys Asp Asn Val Cys Ala Asp Leu His Ile
        290                 295                 300

Gln Asn Lys Thr Asn Cys Pro Ile Ile Asn Ile Arg Cys Asn Asp Lys
305                 310                 315                 320

Cys Tyr Cys Glu Asp Gly Tyr Ala Lys Asp Val Asn Gly Lys Cys Ile
                325                 330                 335

Pro Ile Lys Asp Cys Pro Lys Ile Arg Ser
            340                 345
```

<210> SEQ ID NO 17
<211> LENGTH: 207
<212> TYPE: DNA
<213> ORGANISM: Galleria mellonella
<220> FEATURE:
<221> NAME/KEY: CDS
<222> LOCATION: (1)..(207)
<220> FEATURE:
<221> NAME/KEY: misc_feature
<222> LOCATION: (185)..(185)
<223> OTHER INFORMATION: n is a, c, g, or t

<400> SEQUENCE: 17

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc ttg att aat ata aga tgt aat gac aag tgc tac tgt gaa gat     144
Cys Pro Leu Ile Asn Ile Arg Cys Asn Asp Lys Cys Tyr Cys Glu Asp
        35                  40                  45 ggc tat gca agg gat gtc aat ggc aaa tgt ata ccg ata ana gac tgt     192
Gly Tyr Ala Arg Asp Val Asn Gly Lys Cys Ile Pro Ile Xaa Asp Cys
    50                  55                  60 cct aaa ata cgt tcg                                                 207
Pro Lys Ile Arg Ser
65
```

<210> SEQ ID NO 18
<211> LENGTH: 69
<212> TYPE: PRT
<213> ORGANISM: Galleria mellonella
<220> FEATURE:
<221> NAME/KEY: misc_feature
<222> LOCATION: (62)..(62)

<223> OTHER INFORMATION: The 'Xaa' at location 62 stands for Lys, Arg, Thr, or Ile.

<400> SEQUENCE: 18

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Leu Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Xaa Asp Cys
    50                  55                  60

Pro Lys Ile Arg Ser
65
```

<210> SEQ ID NO 19
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 19

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc atg att aat ata aga tgt aat gac aag tgc tac tgt gaa gat     144
Cys Pro Met Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                  207
Pro Lys Ile Arg Ser
65
```

<210> SEQ ID NO 20
<211> LENGTH: 69
<212> TYPE: PRT
<213> ORGANISM: Galleria mellonella

<400> SEQUENCE: 20

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Met Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 21
<211> LENGTH: 207
<212> TYPE: DNA
<213> ORGANISM: Galleria mellonella

```
<220> FEATURE:
<221> NAME/KEY: CDS
<222> LOCATION: (1)..(207)

<400> SEQUENCE: 21 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc ttc att aat ata aga tgt aat gac aag tgc tac tgt gaa gat     144
Cys Pro Phe Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                 207
Pro Lys Ile Arg Ser
65

<210> SEQ ID NO 22
<211> LENGTH: 69
<212> TYPE: PRT
<213> ORGANISM: Galleria mellonella

<400> SEQUENCE: 22

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Phe Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 23
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 23 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc tgt att aat ata aga tgt aat gac aag tgc tac tgt gaa gat     144
Cys Pro Cys Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                 207
Pro Lys Ile Arg Ser
65
```

```
<210> SEQ ID NO 24
<211> LENGTH: 69
<212> TYPE: PRT
<213> ORGANISM: Galleria mellonella

<400> SEQUENCE: 24

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Cys Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 25
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 25 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc aat att aat ata aga tgt aat gac aag tgc tac tgt gaa gat     144
Cys Pro Asn Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                 207
Pro Lys Ile Arg Ser
65

<210> SEQ ID NO 26
<211> LENGTH: 69
<212> TYPE: PRT
<213> ORGANISM: Galleria mellonella

<400> SEQUENCE: 26

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Asn Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 27
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 27

```
ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
            20                  25                  30 tgt ccc cag att aat ata aga tgt aat gac aag tgc tac tgt gaa gat       144
Cys Pro Gln Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt       192
Gly Tyr Ala Arg Asp Val Asn Gly Lys Cys Ile Pro Ile Lys Asp Cys
    50                  55                  60 cct aaa ata cgt tcg                                                   207
Pro Lys Ile Arg Ser
65
```

<210> SEQ ID NO 28
<211> LENGTH: 69
<212> TYPE: PRT
<213> ORGANISM: Galleria mellonella

<400> SEQUENCE: 28

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Gln Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 29
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 29

```
ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
            20                  25                  30 tgt ccc cac att aat ata aga tgt aat gac aag tgc tac tgt gaa gat       144
Cys Pro His Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt       192
Gly Tyr Ala Arg Asp Val Asn Gly Lys Cys Ile Pro Ile Lys Asp Cys
    50                  55                  60
```

```
cct aaa ata cgt tcg                                                       207
Pro Lys Ile Arg Ser
 65

<210> SEQ ID NO 30
<211> LENGTH: 69
<212> TYPE: PRT
<213> ORGANISM: Galleria mellonella

<400> SEQUENCE: 30

Ile Val Leu Ile Cys Asn Gly Gly His Glu Tyr Tyr Glu Cys Gly Gly
 1               5                  10                  15

Ala Cys Asp Asn Val Cys Ala Asp Leu His Ile Gln Asn Lys Thr Asn
                20                  25                  30

Cys Pro His Ile Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60

Pro Lys Ile Arg Ser
 65

<210> SEQ ID NO 31
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 31 ata gtc cta att tgt aac ggt gga cac gaa tac tac gag tgc ggt gga    48
Ile Val Leu Ile Cys Asn Gly Gly His Glu Tyr Tyr Glu Cys Gly Gly
 1               5                  10                  15 gcc tgc gat aat gta tgt gca gat tta cat ata cag aat aaa aca aac    96
Ala Cys Asp Asn Val Cys Ala Asp Leu His Ile Gln Asn Lys Thr Asn
                20                  25                  30 tgt ccc aag att aat ata aga tgt aat gac aag tgc tac tgt gaa gat   144
Cys Pro Lys Ile Asn Ile Arg Cys Asn Asp Lys Cys Tyr Cys Glu Asp
            35                  40                  45 ggc tat gca agg gat gtc aat ggc aaa tgt ata ccg ata aaa gac tgt   192
Gly Tyr Ala Arg Asp Val Asn Gly Lys Cys Ile Pro Ile Lys Asp Cys
        50                  55                  60 cct aaa ata cgt tcg                                                207
Pro Lys Ile Arg Ser
 65

<210> SEQ ID NO 32
<211> LENGTH: 69
<212> TYPE: PRT
<213> ORGANISM: Galleria mellonella

<400> SEQUENCE: 32

Ile Val Leu Ile Cys Asn Gly Gly His Glu Tyr Tyr Glu Cys Gly Gly
 1               5                  10                  15

Ala Cys Asp Asn Val Cys Ala Asp Leu His Ile Gln Asn Lys Thr Asn
                20                  25                  30

Cys Pro Lys Ile Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60
```

Pro Lys Ile Arg Ser
65

<210> SEQ ID NO 33
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 33

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc cgt att aat ata aga tgt aat gac aag tgc tac tgt gaa gat      144
Cys Pro Arg Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt      192
Gly Tyr Ala Arg Asp Val Asn Gly Lys Cys Ile Pro Ile Lys Asp Cys
    50                  55                  60 cct aaa ata cgt tcg                                                  207
Pro Lys Ile Arg Ser
65
```

<210> SEQ ID NO 34
<211> LENGTH: 69
<212> TYPE: PRT
<213> ORGANISM: Galleria mellonella

<400> SEQUENCE: 34

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Arg Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 35
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 35

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc atc gtt aat ata aga tgt aat gac aag tgc tac tgt gaa gat      144
Cys Pro Ile Val Asn Ile Arg Cys Asn Asp Lys Cys Tyr Cys Glu Asp
        35                  40                  45
```

```
ggc tat gca agg gat gtc aat ggc aaa tgt ata ccg ata aaa gac tgt      192
Gly Tyr Ala Arg Asp Val Asn Gly Lys Cys Ile Pro Ile Lys Asp Cys
    50                  55                  60 cct aaa ata cgt tcg                                                   207
Pro Lys Ile Arg Ser
65

<210> SEQ ID NO 36
<211> LENGTH: 69
<212> TYPE: PRT
<213> ORGANISM: Galleria mellonella

<400> SEQUENCE: 36

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Val Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 37
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 37 ata gtc cta att tgt aac ggt gga cac gaa tac tac gag tgc ggt gga       48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac       96
Ala Cys Asp Asn Val Cys Ala Asp Leu His Ile Gln Asn Lys Thr Asn
            20                  25                  30 tgt ccc atc atg aat ata aga tgt aat gac aag tgc tac tgt gaa gat      144
Cys Pro Ile Met Asn Ile Arg Cys Asn Asp Lys Cys Tyr Cys Glu Asp
        35                  40                  45 ggc tat gca agg gat gtc aat ggc aaa tgt ata ccg ata aaa gac tgt      192
Gly Tyr Ala Arg Asp Val Asn Gly Lys Cys Ile Pro Ile Lys Asp Cys
    50                  55                  60 cct aaa ata cgt tcg                                                   207
Pro Lys Ile Arg Ser
65

<210> SEQ ID NO 38
<211> LENGTH: 69
<212> TYPE: PRT
<213> ORGANISM: Galleria mellonella

<400> SEQUENCE: 38

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Met Asn Ile Arg Cys Asn Asp Lys Cys Tyr Cys Glu Asp
        35                  40                  45
```

Gly Tyr Ala Arg Asp Val Asn Gly Lys Cys Ile Pro Ile Lys Asp Cys
          50                  55                  60

Pro Lys Ile Arg Ser
65

<210> SEQ ID NO 39
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 39 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc atc ttc aat ata aga tgt aat gac aag tgc tac tgt gaa gat     144
Cys Pro Ile Phe Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                  207
Pro Lys Ile Arg Ser
65

<210> SEQ ID NO 40
<211> LENGTH: 69
<212> TYPE: PRT
<213> ORGANISM: Galleria mellonella

<400> SEQUENCE: 40

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Phe Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 41
<211> LENGTH: 207
<212> TYPE: DNA
<213> ORGANISM: Galleria mellonella
<220> FEATURE:
<221> NAME/KEY: CDS
<222> LOCATION: (1)..(207)
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t

<400> SEQUENCE: 41

```
ata gtc nta att tgt anc ggt gga cac gaa tan tnn gng tgc ggt gga      48
Ile Val Xaa Ile Cys Xaa Gly Gly His Glu Xaa Xaa Xaa Cys Gly Gly
1               5                   10                  15 gcc tgc gat aat gta tgt gca gat tta cat ata cag aan naa aca aac      96
Ala Cys Asp Asn Val Cys Ala Asp Leu His Ile Gln Xaa Xaa Thr Asn
            20                  25                  30 tgt ccc atc tgg aat ata aga tgt aat gac aag tgc tac tgt gaa gat     144
Cys Pro Ile Trp Asn Ile Arg Cys Asn Asp Lys Cys Tyr Cys Glu Asp
        35                  40                  45 ggc tat gca agg gat gtc aat ggc aaa tgt ata ccg att aan gnn tgt     192
Gly Tyr Ala Arg Asp Val Asn Gly Lys Cys Ile Pro Ile Xaa Xaa Cys
    50                  55                  60 cct aaa ata cgt tcg                                                  207
Pro Lys Ile Arg Ser
65
```

<210> SEQ ID NO 42
<211> LENGTH: 69
<212> TYPE: PRT
<213> ORGANISM: Galleria mellonella
<220> FEATURE:
<221> NAME/KEY: misc_feature
<222> LOCATION: (3)..(3)
<223> OTHER INFORMATION: The 'Xaa' at location 3 stands for Ile, Val, or
      Leu.
<220> FEATURE:
<221> NAME/KEY: misc_feature
<222> LOCATION: (6)..(6)
<223> OTHER INFORMATION: The 'Xaa' at location 6 stands for Asn, Ser,
      Thr, or Ile.
<220> FEATURE:
<221> NAME/KEY: misc_feature
<222> LOCATION: (11)..(11)
<223> OTHER INFORMATION: The 'Xaa' at location 11 stands for Tyr.
<220> FEATURE:
<221> NAME/KEY: misc_feature
<222> LOCATION: (12)..(12)
<223> OTHER INFORMATION: The 'Xaa' at location 12 stands for Tyr, Trp,
      Cys, Ser, Leu, or Phe.
<220> FEATURE:
<221> NAME/KEY: misc_feature
<222> LOCATION: (13)..(13)
<223> OTHER INFORMATION: The 'Xaa' at location 13 stands for Glu, Gly,
      Ala, or Val.
<220> FEATURE:
<221> NAME/KEY: misc_feature
<222> LOCATION: (29)..(29)
<223> OTHER INFORMATION: The 'Xaa' at location 29 stands for Lys, or
      Asn.

```
<220> FEATURE:
<221> NAME/KEY: misc_feature
<222> LOCATION: (30)..(30)
<223> OTHER INFORMATION: The 'Xaa' at location 30 stands for Lys, Glu,
      or Gln.
<220> FEATURE:
<221> NAME/KEY: misc_feature
<222> LOCATION: (62)..(62)
<223> OTHER INFORMATION: The 'Xaa' at location 62 stands for Lys, or
      Asn.
<220> FEATURE:
<221> NAME/KEY: misc_feature
<222> LOCATION: (63)..(63)
<223> OTHER INFORMATION: The 'Xaa' at location 63 stands for Glu, Asp,
      Gly, Ala, or Val.

<400> SEQUENCE: 42

Ile Val Xaa Ile Cys Xaa Gly Gly His Glu Xaa Xaa Xaa Cys Gly Gly
1               5                   10                  15

Ala Cys Asp Asn Val Cys Ala Asp Leu His Ile Gln Xaa Xaa Thr Asn
            20                  25                  30

Cys Pro Ile Trp Asn Ile Arg Cys Asn Asp Lys Cys Tyr Cys Glu Asp
        35                  40                  45

Gly Tyr Ala Arg Asp Val Asn Gly Lys Cys Ile Pro Ile Xaa Xaa Cys
    50                  55                  60

Pro Lys Ile Arg Ser
65

<210> SEQ ID NO 43
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 43 ata gtc cta att tgt aac ggt gga cac gaa tac tac gag tgc ggt gga     48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac     96
Ala Cys Asp Asn Val Cys Ala Asp Leu His Ile Gln Asn Lys Thr Asn
            20                  25                  30 tgt ccc atc tac aat ata aga tgt aat gac aag tgc tac tgt gaa gat    144
Cys Pro Ile Tyr Asn Ile Arg Cys Asn Asp Lys Cys Tyr Cys Glu Asp
        35                  40                  45 ggc tat gca agg gat gtc aat ggc aaa tgt ata ccg ata aaa gac tgt    192
Gly Tyr Ala Arg Asp Val Asn Gly Lys Cys Ile Pro Ile Lys Asp Cys
    50                  55                  60 cct aaa ata cgt tcg                                                 207
Pro Lys Ile Arg Ser
65

<210> SEQ ID NO 44
<211> LENGTH: 69
<212> TYPE: PRT
<213> ORGANISM: Galleria mellonella

<400> SEQUENCE: 44

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Tyr Asn Ile Arg Cys Asn Asp Lys Cys Tyr Cys Glu Asp
```

-continued

```
                35                  40                  45
Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 45
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 45

```
ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
                20                  25                  30 tgt ccc atc agt aat ata aga tgt aat gac aag tgc tac tgt gaa gat       144
Cys Pro Ile Ser Asn Ile Arg Cys Asn Asp Lys Cys Tyr Cys Glu Asp
            35                  40                  45 ggc tat gca agg gat gtc aat ggc aaa tgt ata ccg ata aaa gac tgt       192
Gly Tyr Ala Arg Asp Val Asn Gly Lys Cys Ile Pro Ile Lys Asp Cys
        50                  55                  60 cct aaa ata cgt tcg                                                    207
Pro Lys Ile Arg Ser
65
```

<210> SEQ ID NO 46
<211> LENGTH: 69
<212> TYPE: PRT
<213> ORGANISM: Galleria mellonella

<400> SEQUENCE: 46

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
                20                  25                  30

Cys Pro Ile Ser Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60

Pro Lys Ile Arg Ser
65
```

<210> SEQ ID NO 47
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 47

```
ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
```

```
                    20                  25                  30
tgt ccc atc act aat ata aga tgt aat gac aag tgc tac tgt gaa gat        144
Cys Pro Ile Thr Asn Ile Arg Cys Asn Asp Lys Cys Tyr Cys Glu Asp
            35                  40                  45 ggc tat gca agg gat gtc aat ggc aaa tgt ata ccg ata aaa gac tgt        192
Gly Tyr Ala Arg Asp Val Asn Gly Lys Cys Ile Pro Ile Lys Asp Cys
        50                  55                  60 cct aaa ata cgt tcg                                                    207
Pro Lys Ile Arg Ser
65
```

<210> SEQ ID NO 48
<211> LENGTH: 69
<212> TYPE: PRT
<213> ORGANISM: Galleria mellonella

<400> SEQUENCE: 48

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Thr Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 49
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 49

```
ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
            20                  25                  30 tgt ccc atc aat aat ata aga tgt aat gac aag tgc tac tgt gaa gat        144
Cys Pro Ile Asn Asn Ile Arg Cys Asn Asp Lys Cys Tyr Cys Glu Asp
        35                  40                  45 ggc tat gca agg gat gtc aat ggc aaa tgt ata ccg ata aaa gac tgt        192
Gly Tyr Ala Arg Asp Val Asn Gly Lys Cys Ile Pro Ile Lys Asp Cys
    50                  55                  60 cct aaa ata cgt tcg                                                    207
Pro Lys Ile Arg Ser
65
```

<210> SEQ ID NO 50
<211> LENGTH: 69
<212> TYPE: PRT
<213> ORGANISM: Galleria mellonella

<400> SEQUENCE: 50

```
Ile Val Leu Ile Cys Asn Gly Gly His Glu Tyr Tyr Glu Cys Gly Gly
1               5                   10                  15
```

```
Ala Cys Asp Asn Val Cys Ala Asp Leu His Ile Gln Asn Lys Thr Asn
         20                  25                  30

Cys Pro Ile Asn Ile Arg Cys Asn Asp Lys Cys Tyr Cys Glu Asp
         35                  40                  45

Gly Tyr Ala Arg Asp Val Asn Gly Lys Cys Ile Pro Ile Lys Asp Cys
         50                  55                  60

Pro Lys Ile Arg Ser
65
```

```
<210> SEQ ID NO 51
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 51 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac     96
Ala Cys Asp Asn Val Cys Ala Asp Leu His Ile Gln Asn Lys Thr Asn
                20                  25                  30 tgt ccc atc cag aat ata aga tgt aat gac aag tgc tac tgt gaa gat    144
Cys Pro Ile Gln Asn Ile Arg Cys Asn Asp Lys Cys Tyr Cys Glu Asp
            35                  40                  45 ggc tat gca agg gat gtc aat ggc aaa tgt ata ccg ata aaa gac tgt    192
Gly Tyr Ala Arg Asp Val Asn Gly Lys Cys Ile Pro Ile Lys Asp Cys
        50                  55                  60 cct aaa ata cgt tcg                                                 207
Pro Lys Ile Arg Ser
65
```

```
<210> SEQ ID NO 52
<211> LENGTH: 69
<212> TYPE: PRT
<213> ORGANISM: Galleria mellonella

<400> SEQUENCE: 52

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
                20                  25                  30

Cys Pro Ile Gln Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60

Pro Lys Ile Arg Ser
65
```

```
<210> SEQ ID NO 53
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 53 ata gtc cta att tgt aac ggt gga cac gaa tac tac gag tgc ggt gga      48
Ile Val Leu Ile Cys Asn Gly Gly His Glu Tyr Tyr Glu Cys Gly Gly
```

```
1               5                   10                  15
gcc tgc gat aat gta tgt gca gat tta cat ata cag aat aaa aca aac    96
Ala Cys Asp Asn Val Cys Ala Asp Leu His Ile Gln Asn Lys Thr Asn
             20                  25                  30 tgt ccc atc cat aat ata aga tgt aat gac aag tgc tac tgt gaa gat    144
Cys Pro Ile His Asn Ile Arg Cys Asn Asp Lys Cys Tyr Cys Glu Asp
         35                  40                  45 ggc tat gca agg gat gtc aat ggc aaa tgt ata ccg ata aaa gac tgt    192
Gly Tyr Ala Arg Asp Val Asn Gly Lys Cys Ile Pro Ile Lys Asp Cys
     50                  55                  60 cct aaa ata cgt tcg                                                207
Pro Lys Ile Arg Ser
65

<210> SEQ ID NO 54
<211> LENGTH: 69
<212> TYPE: PRT
<213> ORGANISM: Galleria mellonella

<400> SEQUENCE: 54

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
             20                  25                  30

Cys Pro Ile His Asn Ile Arg Cys Asn Asp Lys Cys Tyr Cys Glu Asp
         35                  40                  45

Gly Tyr Ala Arg Asp Val Asn Gly Lys Cys Ile Pro Ile Lys Asp Cys
     50                  55                  60

Pro Lys Ile Arg Ser
65

<210> SEQ ID NO 55
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 55 ata gtc cta att tgt aac ggt gga cac gaa tac tac gag tgc ggt gga    48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac    96
Ala Cys Asp Asn Val Cys Ala Asp Leu His Ile Gln Asn Lys Thr Asn
             20                  25                  30 tgt ccc atc cgt aat ata aga tgt aat gac aag tgc tac tgt gaa gat    144
Cys Pro Ile Arg Asn Ile Arg Cys Asn Asp Lys Cys Tyr Cys Glu Asp
         35                  40                  45 ggc tat gca agg gat gtc aat ggc aaa tgt ata ccg ata aaa gac tgt    192
Gly Tyr Ala Arg Asp Val Asn Gly Lys Cys Ile Pro Ile Lys Asp Cys
     50                  55                  60 cct aaa ata cgt tcg                                                207
Pro Lys Ile Arg Ser
65

<210> SEQ ID NO 56
<211> LENGTH: 69
<212> TYPE: PRT
<213> ORGANISM: Galleria mellonella

<400> SEQUENCE: 56
```

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Arg Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
            50                  55                  60

Pro Lys Ile Arg Ser
65

<210> SEQ ID NO 57
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 57 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc atc aag aat ata aga tgt aat gac aag tgc tac tgt gaa gat     144
Cys Pro Ile Lys Asn Ile Arg Cys Asn Asp Lys Cys Tyr Cys Glu Asp
            35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
            50                  55                  60 cct aaa ata cgt tcg                                                  207
Pro Lys Ile Arg Ser
65

<210> SEQ ID NO 58
<211> LENGTH: 69
<212> TYPE: PRT
<213> ORGANISM: Galleria mellonella

<400> SEQUENCE: 58

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Lys Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
            50                  55                  60

Pro Lys Ile Arg Ser
65

<210> SEQ ID NO 59
<211> LENGTH: 207
<212> TYPE: DNA
<213> ORGANISM: Galleria mellonella
<220> FEATURE:
<221> NAME/KEY: CDS
<222> LOCATION: (1)..(207)
```

```
<400> SEQUENCE: 59 ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
            20                  25                  30 tgt ccc atc att aat ata gta tgt aat gac aag tgc tac tgt gaa gat       144
Cys Pro Ile Ile Asn Ile Val Cys Asn Asp Lys Cys Tyr Cys Glu Asp
        35                  40                  45 ggc tat gca agg gat gtc aat ggc aaa tgt ata ccg ata aaa gac tgt       192
Gly Tyr Ala Arg Asp Val Asn Gly Lys Cys Ile Pro Ile Lys Asp Cys
    50                  55                  60 cct aaa ata cgt tcg                                                   207
Pro Lys Ile Arg Ser
65

<210> SEQ ID NO 60
<211> LENGTH: 69
<212> TYPE: PRT
<213> ORGANISM: Galleria mellonella

<400> SEQUENCE: 60

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Ile Asn Ile Val Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 61
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 61 ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
            20                  25                  30 tgt ccc atc att aat ata aaa tgt aat gac aag tgc tac tgt gaa gat       144
Cys Pro Ile Ile Asn Ile Lys Cys Asn Asp Lys Cys Tyr Cys Glu Asp
        35                  40                  45 ggc tat gca agg gat gtc aat ggc aaa tgt ata ccg ata aaa gac tgt       192
Gly Tyr Ala Arg Asp Val Asn Gly Lys Cys Ile Pro Ile Lys Asp Cys
    50                  55                  60 cct aaa ata cgt tcg                                                   207
Pro Lys Ile Arg Ser
65

<210> SEQ ID NO 62
<211> LENGTH: 69
```

```
<212> TYPE: PRT
<213> ORGANISM: Galleria mellonella

<400> SEQUENCE: 62

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Ile Ile Asn Ile Lys Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 63
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 63 ata gtc cta att tgt aac ggt gga cac gaa tac tac gag tgc ggt gga        48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac        96
Ala Cys Asp Asn Val Cys Ala Asp Leu His Ile Gln Asn Lys Thr Asn
            20                  25                  30 tgt ccc tgg att aat ata aga tgt aat gac aag tgc tac tgt gaa gat       144
Cys Pro Trp Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt       192
Gly Tyr Ala Arg Asp Val Asn Gly Lys Cys Ile Pro Ile Lys Asp Cys
    50                  55                  60 cct aaa ata cgt tcg                                                    207
Pro Lys Ile Arg Ser
65

<210> SEQ ID NO 64
<211> LENGTH: 69
<212> TYPE: PRT
<213> ORGANISM: Galleria mellonella

<400> SEQUENCE: 64

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Trp Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 65
<211> LENGTH: 207
<212> TYPE: DNA
<213> ORGANISM: Galleria mellonella
```

<220> FEATURE:
<221> NAME/KEY: CDS
<222> LOCATION: (1)..(207)

<400> SEQUENCE: 65

```
ata gtc cta att tgt aac ggt gga cac gaa tac tac gag tgc ggt gga    48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac    96
Ala Cys Asp Asn Val Cys Ala Asp Leu His Ile Gln Asn Lys Thr Asn
                20                  25                  30 tgt ccc tac att aat ata aga tgt aat gac aag tgc tac tgt gaa gat   144
Cys Pro Tyr Ile Asn Ile Arg Cys Asn Asp Lys Cys Tyr Cys Glu Asp
            35                  40                  45 ggc tat gca agg gat gtc aat ggc aaa tgt ata ccg ata aaa gac tgt   192
Gly Tyr Ala Arg Asp Val Asn Gly Lys Cys Ile Pro Ile Lys Asp Cys
        50                  55                  60 cct aaa ata cgt tcg                                                207
Pro Lys Ile Arg Ser
65
```

<210> SEQ ID NO 66
<211> LENGTH: 69
<212> TYPE: PRT
<213> ORGANISM: Galleria mellonella

<400> SEQUENCE: 66

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
                20                  25                  30

Cys Pro Tyr Ile Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60

Pro Lys Ile Arg Ser
65
```

<210> SEQ ID NO 67
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 67

```
ata gtc cta att tgt aac ggt gga cac gaa tac tac gag tgc ggt gga    48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac    96
Ala Cys Asp Asn Val Cys Ala Asp Leu His Ile Gln Asn Lys Thr Asn
                20                  25                  30 tgt ccc atc att aat ata gca tgt aat gac aag tgc tac tgt gaa gat   144
Cys Pro Ile Ile Asn Ile Ala Cys Asn Asp Lys Cys Tyr Cys Glu Asp
            35                  40                  45 ggc tat gca agg gat gtc aat ggc aaa tgt ata ccg ata aaa gac tgt   192
Gly Tyr Ala Arg Asp Val Asn Gly Lys Cys Ile Pro Ile Lys Asp Cys
        50                  55                  60 cct aaa ata cgt tcg                                                207
Pro Lys Ile Arg Ser
65
```

<210> SEQ ID NO 68
<211> LENGTH: 69
<212> TYPE: PRT
<213> ORGANISM: Galleria mellonella

<400> SEQUENCE: 68

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
                20                  25                  30

Cys Pro Ile Ile Asn Ile Ala Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60

Pro Lys Ile Arg Ser
65

<210> SEQ ID NO 69
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 69 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
                20                  25                  30 tgt ccc tgt att aat ata aga tgt aat gac aag tgc tac tgt gaa gat     144
Cys Pro Cys Ile Asn Ile Arg Cys Asn Asp Lys Cys Tyr Cys Glu Asp
            35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
        50                  55                  60 cct aaa ata cgt tcg                                                  207
Pro Lys Ile Arg Ser
65

<210> SEQ ID NO 70
<211> LENGTH: 69
<212> TYPE: PRT
<213> ORGANISM: Galleria mellonella

<400> SEQUENCE: 70

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
                20                  25                  30

Cys Pro Cys Ile Asn Ile Arg Cys Asn Asp Lys Cys Tyr Cys Glu Asp
            35                  40                  45

Gly Tyr Ala Arg Asp Val Asn Gly Lys Cys Ile Pro Ile Lys Asp Cys
        50                  55                  60

Pro Lys Ile Arg Ser
65

<210> SEQ ID NO 71
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 71

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc aag att aat ata aga tgt aat gac aag tgc tac tgt gaa gat     144
Cys Pro Lys Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                  207
Pro Lys Ile Arg Ser
65
```

<210> SEQ ID NO 72
<211> LENGTH: 69
<212> TYPE: PRT
<213> ORGANISM: Galleria mellonella

<400> SEQUENCE: 72

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Lys Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 73
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 73

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc cgt att aat ata aga tgt aat gac aag tgc tac tgt gaa gat     144
Cys Pro Arg Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60
```

```
cct aaa ata cgt tcg                                              207
Pro Lys Ile Arg Ser
65

<210> SEQ ID NO 74
<211> LENGTH: 69
<212> TYPE: PRT
<213> ORGANISM: Galleria mellonella

<400> SEQUENCE: 74

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Arg Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 75
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 75 ata gtc cta att tgt aac ggt gga cac gaa tac tac gag tgc ggt gga   48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac   96
Ala Cys Asp Asn Val Cys Ala Asp Leu His Ile Gln Asn Lys Thr Asn
            20                  25                  30 tgt ccc ttg att aat ata aga tgt aat gac aag tgc tac tgt gaa gat  144
Cys Pro Leu Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt  192
Gly Tyr Ala Arg Asp Val Asn Gly Lys Cys Ile Pro Ile Lys Asp Cys
    50                  55                  60 cct aaa ata cgt tcg                                              207
Pro Lys Ile Arg Ser
65

<210> SEQ ID NO 76
<211> LENGTH: 69
<212> TYPE: PRT
<213> ORGANISM: Galleria mellonella

<400> SEQUENCE: 76

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Leu Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60
```

-continued

Pro Lys Ile Arg Ser
65

<210> SEQ ID NO 77
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 77

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc atg att aat ata aga tgt aat gac aag tgc tac tgt gaa gat     144
Cys Pro Met Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                  207
Pro Lys Ile Arg Ser
65
```

<210> SEQ ID NO 78
<211> LENGTH: 69
<212> TYPE: PRT
<213> ORGANISM: Galleria mellonella

<400> SEQUENCE: 78

```
Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro Met Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65
```

<210> SEQ ID NO 79
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 79

```
ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc ttc att aat ata aga tgt aat gac aag tgc tac tgt gaa gat     144
Cys Pro Phe Ile Asn Ile Arg Cys Asn Asp Lys Cys Tyr Cys Glu Asp
        35                  40                  45
```

```
ggc tat gca agg gat gtc aat ggc aaa tgt ata ccg ata aaa gac tgt    192
Gly Tyr Ala Arg Asp Val Asn Gly Lys Cys Ile Pro Ile Lys Asp Cys
     50                  55                  60 cct aaa ata cgt tcg                                                207
Pro Lys Ile Arg Ser
 65
```

<210> SEQ ID NO 80
<211> LENGTH: 69
<212> TYPE: PRT
<213> ORGANISM: Galleria mellonella

<400> SEQUENCE: 80

```
Ile Val Leu Ile Cys Asn Gly Gly His Glu Tyr Tyr Glu Cys Gly Gly
 1               5                  10                  15

Ala Cys Asp Asn Val Cys Ala Asp Leu His Ile Gln Asn Lys Thr Asn
                20                  25                  30

Cys Pro Phe Ile Asn Ile Arg Cys Asn Asp Lys Cys Tyr Cys Glu Asp
             35                  40                  45

Gly Tyr Ala Arg Asp Val Asn Gly Lys Cys Ile Pro Ile Lys Asp Cys
     50                  55                  60

Pro Lys Ile Arg Ser
 65
```

<210> SEQ ID NO 81
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 81

```
ata gtc cta att tgt aac ggt gga cac gaa tac tac gag tgc ggt gga    48
Ile Val Leu Ile Cys Asn Gly Gly His Glu Tyr Tyr Glu Cys Gly Gly
 1               5                  10                  15 gcc tgc gat aat gta tgt gca gat tta cat ata cag aat aaa aca aac    96
Ala Cys Asp Asn Val Cys Ala Asp Leu His Ile Gln Asn Lys Thr Asn
                20                  25                  30 tgt ccc cag att aat ata aga tgt aat gac aag tgc tac tgt gaa gat    144
Cys Pro Gln Ile Asn Ile Arg Cys Asn Asp Lys Cys Tyr Cys Glu Asp
             35                  40                  45 ggc tat gca agg gat gtc aat ggc aaa tgt ata ccg ata aaa gac tgt    192
Gly Tyr Ala Arg Asp Val Asn Gly Lys Cys Ile Pro Ile Lys Asp Cys
     50                  55                  60 cct aaa ata cgt tcg                                                207
Pro Lys Ile Arg Ser
 65
```

<210> SEQ ID NO 82
<211> LENGTH: 69
<212> TYPE: PRT
<213> ORGANISM: Galleria mellonella

<400> SEQUENCE: 82

```
Ile Val Leu Ile Cys Asn Gly Gly His Glu Tyr Tyr Glu Cys Gly Gly
 1               5                  10                  15

Ala Cys Asp Asn Val Cys Ala Asp Leu His Ile Gln Asn Lys Thr Asn
                20                  25                  30

Cys Pro Gln Ile Asn Ile Arg Cys Asn Asp Lys Cys Tyr Cys Glu Asp
             35                  40                  45
```

```
Gly Tyr Ala Arg Asp Val Asn Gly Lys Cys Ile Pro Ile Lys Asp Cys
            50                  55                  60

Pro Lys Ile Arg Ser
65

<210> SEQ ID NO 83
<211> LENGTH: 207
<212> TYPE: DNA
<213> ORGANISM: Galleria mellonella
<220> FEATURE:
<221> NAME/KEY: CDS
<222> LOCATION: (1)..(207)

<400> SEQUENCE: 83 ata gtc cta att tgt aac ggt gga cac gaa tac tac gag tgc ggt gga      48
Ile Val Leu Ile Cys Asn Gly Gly His Glu Tyr Tyr Glu Cys Gly Gly
1               5                   10                  15 gcc tgc gat aat gta tgt gca gat tta cat ata cag aat aaa aca aac      96
Ala Cys Asp Asn Val Cys Ala Asp Leu His Ile Gln Asn Lys Thr Asn
            20                  25                  30 tgt ccc cac att aat ata aga tgt aat gac aag tgc tac tgt gaa gat     144
Cys Pro His Ile Asn Ile Arg Cys Asn Asp Lys Cys Tyr Cys Glu Asp
        35                  40                  45 ggc tat gca agg gat gtc aat ggc aaa tgt ata ccg ata aaa gac tgt     192
Gly Tyr Ala Arg Asp Val Asn Gly Lys Cys Ile Pro Ile Lys Asp Cys
    50                  55                  60 cct aaa ata cgt tcg                                                 207
Pro Lys Ile Arg Ser
65

<210> SEQ ID NO 84
<211> LENGTH: 69
<212> TYPE: PRT
<213> ORGANISM: Galleria mellonella

<400> SEQUENCE: 84

Ile Val Leu Ile Cys Asn Gly Gly His Glu Tyr Tyr Glu Cys Gly Gly
1               5                   10                  15

Ala Cys Asp Asn Val Cys Ala Asp Leu His Ile Gln Asn Lys Thr Asn
            20                  25                  30

Cys Pro His Ile Asn Ile Arg Cys Asn Asp Lys Cys Tyr Cys Glu Asp
        35                  40                  45

Gly Tyr Ala Arg Asp Val Asn Gly Lys Cys Ile Pro Ile Lys Asp Cys
    50                  55                  60

Pro Lys Ile Arg Ser
65

<210> SEQ ID NO 85
<211> LENGTH: 1041
<212> TYPE: DNA
<213> ORGANISM: Galleria mellonella
<220> FEATURE:
<221> NAME/KEY: CDS
<222> LOCATION: (1)..(1041)

<400> SEQUENCE: 85 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30
```

```
tat gag cgc gat gaa ggt gat aaa tgg cga aac aaa aag ttt gaa ttg      144
Tyr Glu Arg Asp Glu Gly Asp Lys Trp Arg Asn Lys Lys Phe Glu Leu
             35                  40                  45 ggt ttg gag ttt ccc aat ctt cct tat tat att gat ggt gat gtt aaa      192
Gly Leu Glu Phe Pro Asn Leu Pro Tyr Tyr Ile Asp Gly Asp Val Lys
 50                  55                  60 tta aca cag tct atg gcc atc ata cgt tat ata gct gac aag cac aac      240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa      288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt      336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa      384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat      432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat      480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta      528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac      576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc      624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt      672
Thr Phe Gly Gly Gly Asp His Pro Pro Lys Ser Asp Gly Ser Thr Ser
    210                 215                 220 ggt tct ggt cat cac cat cac cat cac tcc gcg ggt ctg gtg cca cgc      720
Gly Ser Gly His His His His His His Ser Ala Gly Leu Val Pro Arg
225                 230                 235                 240 ggt agt act gca att ggt atg aaa gaa acc gct gct gct aaa ttc gaa      768
Gly Ser Thr Ala Ile Gly Met Lys Glu Thr Ala Ala Ala Lys Phe Glu
                245                 250                 255 cgc cag cac atg gac agc cca gat ctg ggt acc ggt ggt tcc ggt           816
Arg Gln His Met Asp Ser Pro Asp Leu Gly Thr Gly Gly Ser Gly
            260                 265                 270 gat gac gac gac aag ata gtc cta att tgt aac ggt gga cac gaa tac      864
Asp Asp Asp Asp Lys Ile Val Leu Ile Cys Asn Gly Gly His Glu Tyr
        275                 280                 285 tac gag tgc ggt gga gcc tgc gat aat gta tgt gca gat tta cat ata      912
Tyr Glu Cys Gly Gly Ala Cys Asp Asn Val Cys Ala Asp Leu His Ile
    290                 295                 300 cag aat aaa aca aac tgt ccc aat att aat ata aga tgt aat gac aag      960
Gln Asn Lys Thr Asn Cys Pro Asn Ile Asn Ile Arg Cys Asn Asp Lys
305                 310                 315                 320 tgc tac tgt gaa gat ggc tat gca agg gat gtc aat ggc aaa tgt ata     1008
Cys Tyr Cys Glu Asp Gly Tyr Ala Arg Asp Val Asn Gly Lys Cys Ile
                325                 330                 335 ccg ata aaa gac tgt cct aaa ata cgt tcg tag                          1041
Pro Ile Lys Asp Cys Pro Lys Ile Arg Ser
```

<210> SEQ ID NO 86
<211> LENGTH: 346
<212> TYPE: PRT
<213> ORGANISM: Galleria mellonella

<400> SEQUENCE: 86

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Ile Val Leu Ile Cys Asn Gly His Glu Tyr
        275                 280                 285

Tyr Glu Cys Gly Gly Ala Cys Asp Asn Val Cys Ala Asp Leu His Ile
    290                 295                 300

Gln Asn Lys Thr Asn Cys Pro Asn Ile Asn Ile Arg Cys Asn Asp Lys
305                 310                 315                 320

Cys Tyr Cys Glu Asp Gly Tyr Ala Arg Asp Val Asn Gly Lys Cys Ile
                325                 330                 335

Pro Ile Lys Asp Cys Pro Lys Ile Arg Ser
            340                 345

<210> SEQ ID NO 87
<211> LENGTH: 1041

```
<212> TYPE: DNA
<213> ORGANISM: Galleria mellonella
<220> FEATURE:
<221> NAME/KEY: CDS
<222> LOCATION: (1)..(1041)

<400> SEQUENCE: 87 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc     624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt     672
Thr Phe Gly Gly Gly Asp His Pro Pro Lys Ser Asp Gly Ser Thr Ser
    210                 215                 220 ggt tct ggt cat cac cat cac cat cac tcc gcg ggt ctg gtg cca cgc     720
Gly Ser Gly His His His His His His Ser Ala Gly Leu Val Pro Arg
225                 230                 235                 240 ggt agt act gca att ggt atg aaa gaa acc gct gct gct aaa ttc gaa     768
Gly Ser Thr Ala Ile Gly Met Lys Glu Thr Ala Ala Ala Lys Phe Glu
                245                 250                 255 cgc cag cac atg gac agc cca gat ctg ggt acc ggt ggc tcc ggt         816
Arg Gln His Met Asp Ser Pro Asp Leu Gly Thr Gly Gly Ser Gly
            260                 265                 270 gat gac gac gac aag ata gtc cta att tgt aac ggt gga cac gaa tac     864
Asp Asp Asp Asp Lys Ile Val Leu Ile Cys Asn Gly Gly His Glu Tyr
        275                 280                 285
```

```
tac gag tgc ggt gga gcc tgc gat aat gta tgt gca gat tta cat ata      912
Tyr Glu Cys Gly Gly Ala Cys Asp Asn Val Cys Ala Asp Leu His Ile
    290             295                 300 cag aat aaa aca aac tgt ccc atc agt aat ata aga tgt aat gac aag      960
Gln Asn Lys Thr Asn Cys Pro Ile Ser Asn Ile Arg Cys Asn Asp Lys
305             310                 315                 320 tgc tac tgt gaa gat ggc tat gca agg gat gtc aat ggc aaa tgt ata     1008
Cys Tyr Cys Glu Asp Gly Tyr Ala Arg Asp Val Asn Gly Lys Cys Ile
                325                 330                 335 ccg ata aaa gac tgt cct aaa ata cgt tcg tag                         1041
Pro Ile Lys Asp Cys Pro Lys Ile Arg Ser
            340                 345

<210> SEQ ID NO 88
<211> LENGTH: 346
<212> TYPE: PRT
<213> ORGANISM: Galleria mellonella

<400> SEQUENCE: 88

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
            260                 265                 270

Asp Asp Asp Asp Lys Ile Val Leu Ile Cys Asn Gly Gly His Glu Tyr
        275                 280                 285
```

| | | | | | | | | | | | | |
|---|---|---|---|---|---|---|---|---|---|---|---|---|
| Tyr | Glu | Cys | Gly | Gly | Ala | Cys | Asp | Asn | Val | Cys | Ala | Asp | Leu | His | Ile |
| | 290 | | | | | 295 | | | | 300 | | | | | |

| | | | | | | | | | | | | | | | |
|---|---|---|---|---|---|---|---|---|---|---|---|---|---|---|---|
| Gln | Asn | Lys | Thr | Asn | Cys | Pro | Ile | Ser | Asn | Ile | Arg | Cys | Asn | Asp | Lys |
| 305 | | | | | 310 | | | | | 315 | | | | | 320 |

| | | | | | | | | | | | | | | | |
|---|---|---|---|---|---|---|---|---|---|---|---|---|---|---|---|
| Cys | Tyr | Cys | Glu | Asp | Gly | Tyr | Ala | Arg | Asp | Val | Asn | Gly | Lys | Cys | Ile |
| | | | | 325 | | | | | 330 | | | | | 335 | |

| | | | | | | | |
|---|---|---|---|---|---|---|---|
| Pro | Ile | Lys | Asp | Cys | Pro | Lys | Ile | Arg | Ser |
| | | 340 | | | | | 345 | |

<210> SEQ ID NO 89
<211> LENGTH: 1041
<212> TYPE: DNA
<213> ORGANISM: Galleria mellonella
<220> FEATURE:
<221> NAME/KEY: CDS
<222> LOCATION: (1)..(1041)

<400> SEQUENCE: 89

```
atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac     576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc     624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt     672
Thr Phe Gly Gly Gly Asp His Pro Pro Lys Ser Asp Gly Ser Thr Ser
    210                 215                 220
```

```
ggt tct ggt cat cac cat cac cat cac tcc gcg ggt ctg gtg cca cgc      720
Gly Ser Gly His His His His His His Ser Ala Gly Leu Val Pro Arg
225             230                 235                 240 ggt agt act gca att ggt atg aaa gaa acc gct gct gct aaa ttc gaa      768
Gly Ser Thr Ala Ile Gly Met Lys Glu Thr Ala Ala Ala Lys Phe Glu
                245                 250                 255 cgc cag cac atg gac agc cca gat ctg ggt acc ggt ggc tcc ggt          816
Arg Gln His Met Asp Ser Pro Asp Leu Gly Thr Gly Gly Ser Gly
            260                 265                 270 gat gac gac gac aag ata gtc cta att tgt aac ggt gga cac gaa tac      864
Asp Asp Asp Asp Lys Ile Val Leu Ile Cys Asn Gly Gly His Glu Tyr
            275                 280                 285 tac gag tgc ggt gga gcc tgc gat aat gta tgt gca gat tta cat ata      912
Tyr Glu Cys Gly Gly Ala Cys Asp Asn Val Cys Ala Asp Leu His Ile
        290                 295                 300 cag aat aaa aca aac tgt ccc atc att aat ata aaa tgt aat gac aag      960
Gln Asn Lys Thr Asn Cys Pro Ile Ile Asn Ile Lys Cys Asn Asp Lys
305             310                 315                 320 tgc tac tgt gaa gat ggc tat gca agg gat gtc aat ggc aaa tgt ata     1008
Cys Tyr Cys Glu Asp Gly Tyr Ala Arg Asp Val Asn Gly Lys Cys Ile
                325                 330                 335 ccg ata aaa gac tgt cct aaa ata cgt tcg tag                         1041
Pro Ile Lys Asp Cys Pro Lys Ile Arg Ser
            340                 345
```

<210> SEQ ID NO 90
<211> LENGTH: 346
<212> TYPE: PRT
<213> ORGANISM: Galleria mellonella

<400> SEQUENCE: 90

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

-continued

Thr Phe Gly Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Lys Phe Glu
                245                 250                 255

Arg Gln His Met Asp Ser Pro Asp Leu Gly Thr Gly Gly Ser Gly
            260                 265                 270

Asp Asp Asp Asp Lys Ile Val Leu Ile Cys Asn Gly Gly His Glu Tyr
        275                 280                 285

Tyr Glu Cys Gly Gly Ala Cys Asp Asn Val Cys Ala Asp Leu His Ile
    290                 295                 300

Gln Asn Lys Thr Asn Cys Pro Ile Ile Asn Ile Lys Cys Asn Asp Lys
305                 310                 315                 320

Cys Tyr Cys Glu Asp Gly Tyr Ala Arg Asp Val Asn Gly Lys Cys Ile
                325                 330                 335

Pro Ile Lys Asp Cys Pro Lys Ile Arg Ser
            340                 345

<210> SEQ ID NO 91
<211> LENGTH: 1041
<212> TYPE: DNA
<213> ORGANISM: Galleria mellonella
<220> FEATURE:
<221> NAME/KEY: CDS
<222> LOCATION: (1)..(1041)

<400> SEQUENCE: 91

```
atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat     480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta     528
```

```
                Val Val Leu Tyr Met Asp Pro Met Cys Leu Asp Ala Phe Pro Lys Leu
                                165                 170                 175 gtt tgt ttt aaa aaa cgt att gaa gct atc cca caa att gat aag tac          576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc          624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ggt tca act agt          672
Thr Phe Gly Gly Gly Asp His Pro Pro Lys Ser Asp Gly Ser Thr Ser
    210                 215                 220 ggt tct ggt cat cac cat cac cat cac tcc gcg ggt ctg gtg cca cgc          720
Gly Ser Gly His His His His His His Ser Ala Gly Leu Val Pro Arg
225                 230                 235                 240 ggt agt act gca att ggt atg aaa gaa acc gct gct gct aaa ttc gaa          768
Gly Ser Thr Ala Ile Gly Met Lys Glu Thr Ala Ala Ala Lys Phe Glu
                245                 250                 255 cgc cag cac atg gac agc cca gat ctg ggt acc ggt ggt ggc tcc ggt          816
Arg Gln His Met Asp Ser Pro Asp Leu Gly Thr Gly Gly Gly Ser Gly
            260                 265                 270 gat gac gac gac aag ata gtc cta att tgt aac ggt gga cac gaa tac          864
Asp Asp Asp Asp Lys Ile Val Leu Ile Cys Asn Gly Gly His Glu Tyr
        275                 280                 285 tac gag tgc ggt gga gcc tgc gat aat gta tgt gca gat tta cat ata          912
Tyr Glu Cys Gly Gly Ala Cys Asp Asn Val Cys Ala Asp Leu His Ile
    290                 295                 300 cag aat aaa aca aac tgt ccc tgt att aat ata aga tgt aat gac aag          960
Gln Asn Lys Thr Asn Cys Pro Cys Ile Asn Ile Arg Cys Asn Asp Lys
305                 310                 315                 320 tgc tac tgt gaa gat ggc tat gca agg gat gtc aat ggc aaa tgt ata         1008
Cys Tyr Cys Glu Asp Gly Tyr Ala Arg Asp Val Asn Gly Lys Cys Ile
                325                 330                 335 ccg ata aaa gac tgt cct aaa ata cgt tcg tag                             1041
Pro Ile Lys Asp Cys Pro Lys Ile Arg Ser
            340                 345
```

<210> SEQ ID NO 92
<211> LENGTH: 346
<212> TYPE: PRT
<213> ORGANISM: Galleria mellonella

<400> SEQUENCE: 92

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
            260                 265                 270

Asp Asp Asp Asp Lys Ile Val Leu Ile Cys Asn Gly Gly His Glu Tyr
            275                 280                 285

Tyr Glu Cys Gly Gly Ala Cys Asp Asn Val Cys Ala Asp Leu His Ile
    290                 295                 300

Gln Asn Lys Thr Asn Cys Pro Cys Ile Asn Ile Arg Cys Asn Asp Lys
305                 310                 315                 320

Cys Tyr Cys Glu Asp Gly Tyr Ala Arg Asp Val Asn Gly Lys Cys Ile
                325                 330                 335

Pro Ile Lys Asp Cys Pro Lys Ile Arg Ser
                340                 345
```

<210> SEQ ID NO 93
<211> LENGTH: 57
<212> TYPE: DNA
<213> ORGANISM: Galleria mellonella
<220> FEATURE:
<221> NAME/KEY: CDS
<222> LOCATION: (1)..(57)

<400> SEQUENCE: 93

```
atg aag tgc tta tta tat tta tgt cta tgg tgt tat tgt gta cta gta      48
Met Lys Cys Leu Leu Tyr Leu Cys Leu Trp Cys Tyr Cys Val Leu Val
1               5                   10                  15 agc agt agc                                                           57
Ser Ser Ser
```

<210> SEQ ID NO 94
<211> LENGTH: 19
<212> TYPE: PRT
<213> ORGANISM: Galleria mellonella

<400> SEQUENCE: 94

```
Met Lys Cys Leu Leu Tyr Leu Cys Leu Trp Cys Tyr Cys Val Leu Val
1               5                   10                  15

Ser Ser Ser
```

<210> SEQ ID NO 95
<211> LENGTH: 55
<212> TYPE: PRT
<213> ORGANISM: Solenopsis
<220> FEATURE:

```
<221> NAME/KEY: PEPTIDE
<222> LOCATION: (1)..(55)

<400> SEQUENCE: 95

Cys Asn Arg Glu Asn Glu Glu Tyr Gln Cys Gly Ser Ala Cys Gln Thr
1               5                   10                  15

Thr Cys Thr Asn Leu Gly Gln Asn Cys Ser Ile Ile Asn Ile Arg Cys
            20                  25                  30

Asn Asp Ala Cys Tyr Cys Lys Pro Gly Tyr Ala Arg Met Gly Gly Asp
        35                  40                  45

Ser Ser Pro Cys Ile Pro Ile
    50                  55
```

USE OF METALLOPROTEINASE INHIBITORS AGAINST BACTERIAL INFECTIONS

CROSS REFERENCE TO RELATED APPLICATIONS

This is a national phase application of international patent application no. PCT/EP2015/065210, filed on Jul. 3, 2015, which itself claims priority to European application EP14175566.0, filed Jul. 3, 2014. All of the applications referred to in this paragraph are incorporated by reference in their entireties herein.

REFERENCE TO SEQUENCE LISTING SUBMITTED ELECTRONICALLY

The official copy of the sequence listing is submitted electronically via EFS-Web as an ASCII formatted sequence listing with file "EP14175566_SEQID" created on Dec. 28, 2016, and having a size of 138 Kilobytes. The sequence listing contained in this ASCII formatted document forms part of the specification and is herein incorporated by reference in its entirety.

FIELD OF THE INVENTION

This invention relates to combinations of molecules, nucleic acids, peptides and proteins inhibiting growth of resistant bacteria, and to the use of peptides or nuclear acids and their combinations with molecules and proteins inhibiting protease activity, growth of pathogens and formation of biofilms. More specifically, the invention relates to combinations of molecules, nucleic acids, peptides and proteins, and the use of nucleic acids, peptides and their combinations with molecules and proteins exhibiting activity against a spectrum of proteases of microbial or fungal origin, in particular against the metzincin family including thermolysin, anthrax neutral protease 599 (npr599), pseudolysin, and aureolysin, bacterial growth, especially in planktonic free and aggregate form, and the formation of bacterial biofilms. The invention relates further to pharmaceutical compositions comprising the molecules, nucleic acids, peptides or proteins, including compositions comprising additionally molecules of antibiotic activity. The invention also relates to methods of using the peptides or nucleic acids and their combinations with molecules and proteins to prevent and/or treat bacterial or fungal infections and their symptoms, including the reduction of toxic effects of secreted or membrane bound bacterial proteases such as aureolysin, bacillolysin, pseudolysin, vibriolysin, and anthrax npr599 by inhibiting their respective proteolytic activity, and to render biofilm protected or resistant bacteria susceptible for the effects of antibiotics. The inventions further relates to using the peptides or nucleic acids and their combinations with molecules and proteins at any stage of a bacterial infection, especially at early stages.

BACKGROUND OF THE INVENTION

Current standard treatments for bacterial infection rely predominantly on antibiotics. Under certain conditions, however, the use of antibiotics provoques the emergence or selection of resistant bacterial strains. Even worse, some bacterial strains are capable of developing resistance against entire panels of antibiotics. Therefore several programs have been launched to develop new companion compounds targeting bacterial virulence.

The mode of action of most antibiotics relies on the disruption of the bacterial growth cycle by preventing the synthesis or assembly of key components of bacterial processes such as cell wall synthesis, DNA replication and protein synthesis. Antibiotics are highly effective unless pathogens have become resistant against one or even multiple antibiotics. Today, multiresistant bacteria pose a major clinical problem and health threat (Health Care-Associated Infections, HAI). Infections due to antibiotic resistant microorganisms lead to significantly higher morbidity, longer hospitalization, increased mortality rates and increased health care costs. Especially the so called "ESKAPE" pathogens (*Enterococcus faecium, Staphylococcus aureus, Klebsiella pneumonia, Acinetobacter baumannii, Pseudomonas aeruginosa*, and *Enterobacter* species) represent a major harm to patients in hospitals. About 440,000 estimated HA infections among US adult inpatients annually result in additional healthcare cost of $9.8 billion dollar every year (Zimlichman et al. 2013).

Many nosocomial infections are caused by *pseudomonas aeruginosa* which is responsible for 10% of all hospital acquired infections (Aloush et al 2006). Infections caused by this microorganism are often life threatening and difficult to treat due to its low susceptibility to antimicrobial agents and to the frequent emergence of antibiotic resistance during therapy. These strains are sensitive to just a few antibiotic agents like cephalosporins, carbenicillin, colistin, gentamycin, polymyxin, quinolones and streptomycin (Sivanmaliappan et al 2011). Their prominent drug resistance results from de novo emergence of resistance after exposure to antimicrobials, and patient-to-patient contamination with resistant *P. aeruginosa*. Practically all known mechanisms of antimicrobial resistance can be observed, like: derepression of chromosomal AmpC cephalosporinase; production of plasmid or integrin mediated β lactamases from different molecular classes (carbenicillinases and extended spectrum β lactamases belonging to class A, class D oxacillinases and class B carbapenem hydrolysing enzymes); diminished outer membrane permeability (loss of OprD proteins); overexpression of active efflux systems with wide substrate profiles; synthesis of aminoglycoside modifying enzymes (phosphoryltransferases, acetyltransferases and adenylyltransferases); and structural alterations of topoisomerases II and IV determining quinolone resistance. Worryingly these mechanisms are often simultaneously developed and activated, thereby conferring multiresistant phenotypes, rendering this microbe less amenable to control in hospitals (Strateva et al 2009). According to data from the US Centers for Disease Control and Prevention and the National Nosocomial Infection Surveilance System, *P. aeruginosa* is the second most common cause of nosocomial pneumonia (17%), the third most common cause of urinary tract infections (7%), the fourth most common cause of surgical site infection (8%), the seventh most frequently isolated pathogen from the bloodstream (2%) and the fifth most common isolate (9%) overall from all sites (El Solh et al 2009). More importantly, it is the most common multidrug resistant Gram negative pathogen causing pneumonia in hospitalized patients.

To support the therapy of bacterial infections, bacterial virulence factors have become targets for reducing the symptoms of bacterial infections. Being essential for maintaining bacterial pathogenicity, virulence factors promote i.a. resistance to environmental threats and to host defense mechanisms, growth capability, adherence to the host, tissue specificity, and access to nutrition resources. A variety of bacterial and often strain specific components are involved, many of them harmful to the host. The coordinated function of virulence factors determines the aggressiveness of the strain. In many cases virulence factors are secreted proteins or enzymes, sometimes exhibiting very specific functions. For example, one of the most toxic bacterial virulence factors is the so called Lambda-toxin (light chain) secreted by *Clostridium botulinum*. The zinc-dependent protease is a thermolysin like protease (TLP) targeting synaptic vesicle fusion proteins and causing severe neurotoxic effects with a lethal dose as low eight nanograms per kilogram of body weight (Lebrun et al 2009). TLPs are present in many microorganism species, and many TLPs are regarded as key pathogenic factors involved in several severe bacterial infections. For example, Lambda-toxin from *Clostridium perfringens* degrades various human immune defense proteins. Vibriolysin from *Vibrio* spec. and Pseudolysin from *Pseudomonas aeruginosa* are potentially lethal blood-poisons in humans. Furthermore, *Bacillus anthracis* also disposes of potent metalloproteases.

Pseudosysin, aureolysin, bacillolysin, pseudolysin, vibriolysin, and anthrax npr599 belong to the M4 or metzincin family of metalloproteinases for which mammals and many invertebrates lack specific inhibitors. These proteases are presumably at the origin of many pathological symptoms associated with severe infections such as septicemia, hemorrhagic tissue bleeding, necrosis and enhancement of vascular permeability (Chung et al. 2006). Severe diseases like gastric and peptic ulcers and gastric carcinoma originate at least partly from the effect of pathogen M4 metalloproteinases (Schmidtchen et al. 2003, Smith et al. 1994).

Some virulence factors were recently recognized as putative targets for drug design and therapeutic intervention. While many newly discovered synthetic or natural small organic compounds exhibit anti virulence activity, antibodies neutralizing bacterial toxins are in the focus of current ant virulence strategies in industry. An example for this approach is the Humaneered® PEGylated, recombinant anti-*Pseudomonas*-PcrV antibody Fab' fragment (KB001) that inhibits the function of the *Pseudomonas aeruginosa* type III secretion system (TTSS) (Milla et al. 2013). The PEGylation extends serum half-life and also protects against inactivation by proteases (mostly Pseudolysin) secreted by *Pseudomonas aeruginosa* at the target site. A clinical phase I/II trial for pneumonia prevention is currently ongoing. Another example is KBSA 301 from Kenta Biotech, a fully human IgG1 antibody highly specific for *S. aureus* exotoxin being active against MRSA and MSSA.

Inhibitors of pseudolysin were also identified and published. It was assumed that pseudolysin inhibitors could interfere with biofilm formation and preservation. Thus, all published in vitro tests were carried out as biofilm interference tests of *pseudomonas* a. N-mercaptoacetyl-Phe-Tyr-amide (K(i)=41 nM) (Cathgart G. R. et al, 2011), phosphoramidon, a compound produced by the Bacterium *Streptomyces tanashiensis*, and its derivative talopeptin, phosphonomadites, phenanthroline, and small molecules on a quinazolin basis (Khan et al 2009) all target pseudolysin, but also physiological M4 family related proteases of the host. Phosphoramidon, for example, is inhibiting the endogenous protein endothelin converting enzyme (ECE). These side effects are probably the main reason why none of these compounds was investigated further in clinical trials so far.

Cathgart et al. (2011) observed that a number of pseudolysin inhibitors can reduce already formed *pseudomonas* a. biofilms, whearas planktonic pseudomona a. was not at all affected by said inhibitors. They further observed that biofilms could be completely dissolved when said inhibitors were combined with antibiotics like gentamycin or ciprofloxacin, and both, inhibitor and antibiotic, were applied at high doses.

Popov et al. (Popov S. G. et al, 2005) published results of an experiment on the simultaneous application of an antibiotic compound (Ciprofloxacin, Bayer Healthcare AG) and metalloprotease inhibitors like phenanthroline and phosphoramidon in mice. They found that the two metalloproteinase inhibitors exerted an additional inhibition on the infectious strain, but only when applied with a delay of one or two days after the animal was challenged of with bacterial spores, and not immediately after the challenge. Immediate application of the inhibitor combination, however, resulted in just an insignificant difference in comparison to applying ciprofloxacin alone. Moreover the authors observed that applying pseudolysin inhibitors alone, i.e. without antibiotics in parallel, had no effect. These observations reflect the general expectation that the therapeutic effect of M4 protease inhibitors is limited to late infection stages when biofilms start forming and pseudolysin is shed. At these stages, a high dosis of both, inbitors and antibiotics, is expected to show strong inhibition of bacterial growth.

A particular peptide inhibiting thermolysin-like enzymes is the insect metalloproteinase inhibitor IMPIα. It was originally discovered in and purified from the hemolymph of immunized *G. mellonella* larvae (Wedde et al. 1998). Its active moiety comprises 69 amino acids including intramolecular cystein bonds, and a molecular weight of 7667.7 Da. The molecule has a reported IC60 of 0.62, 0.86 and only 81.66 nM for thermolysin, bacillolysin and pseudolysin, respectively. IMPIα was tested against human metallomatrix proteases MMP1, 2, 3, 7, 8, and -9, of which only MMP1 and MMP2 showed a negligible inhibition. From this comparison it was further deduced that an active site loop would be present in IMPIα between aa 33-aa40, including a cleavage site between aa37 (Asparagine) and aa38 (Isoleucin). Other known protein inhibitors of metalloproteinases do not inhibit proteinases of the M4 protease family. It was shown that IMPIα can be produced recombinantly in bacteria, especially in *E. coli*. Eukaryotic cells such as CHO cells, transgenic plants and animals may also serve as sources for recombinant production. Alternatively, chemical synthesis of molecules and cell free recombinant production could also be means to produce IMPIα.

Vilcinskas A (2011) discloses in a review "Anti-Infective therapeutics from the lepidopteran model host *Galleria mellonella*" Current Pharmaceutical Design 17(13), 1240-124 that the larvae of the greater wax moth *Galleria mellonella* prosper in use both as surrogate alternative model hosts for human pathogens and as a whole-animal-high-throughput-system for in vivo testing of antibiotics or mutantlibraries of pathogens. In addition, a broad spectrum of antimicrobial peptides and proteins has been identified in this insect during the past decade among which some appear to be specific for Lepidoptera. Its arsenal of immunity-related effector molecules encompasses peptides and proteins exhibiting potent activity against bacteria, fungi or both, whose potential as new anti-infective therapeutics is presently being explored. Of particular interest is the insect metalloproteinase inhibitor (IMPI) which has been discovered in *G. mellonella*. The IMPI exhibits a specific and potent activity against thermolysin-like microbial metalloproteinases including a number of prominent virulence and/or pathogenic factors of human pathogens which are responsible for severe symptoms such as septicemia, hemorrhagic tissue bleeding, necrosis and enhancement of vascular permeability. The IMPI and antimicrobial peptides from *G. mellonella* may provide promising templates for the rational design of new drugs since evidence is available that the combination of antibiotics with inhibitors of pathogen-associated proteolytic enzymes yields synergistic therapeutic effects. The potential and limitations of insect-derived geneencoded antimicrobial compounds as antiinfective therapeutics are discussed.

Anja Clermont, et al discloses in Biochemical Journal August 2004, 382 (1) 315-322, in an article "Cloning and expression of an inhibitor of microbial metalloproteinases from insects contributing to innate immunity" that the first IMPI (inhibitor of metalloproteinases from insects) was identified in the greater wax moth, *Galleria mellonella*. They report cloning and expression of a cDNA coding for this IMPI. The IMPI mRNA was identified among the induced transcripts from a subtractive and suppressive PCR analysis after bacterial challenge of *G. mellonella* larvae. Induced expression of the IMPI during a humoral immune response was confirmed by realtime PCR, which documented up to 500 times higher amounts of IMPI mRNA in immunized larvae in comparison with untreated ones. The IMPI sequence shares no similarity with those of tissue inhibitors of metalloproteinases or other natural inhibitors of metalloproteinases, and the recombinant IMPI specifically inhibits thermolysin-like metalloproteinases, but not matrix metalloproteinases. These results support the hypothesis that the IMPI represents a novel type of immune-related protein which is induced and processed during the *G. mellonella* humoral immune response to inactivate pathogen-associated thermolysin-like metalloproteinases.

R. Caldwell et al. report in 2003 Wiley Periodicals, Inc. J Biomed Mater Res 67A: 1-10, 2003 about "Significant occurrences of arterial restenosis remain a complicating factor of endovascular stent implantation." The incorporation of GM6001, a matrix metalloproteinase inhibitor (MMPI), into a poly(lactide-co-glycolide) (PLGA) absorbable coating for 316L stainless steel is proposed as a means to reduce the rate of smooth muscle cell proliferation and migration. Coatings were fabricated using a solvent evaporation technique, and the surfaces were characterized by noncontacting profilometry and scanning electron microscopy. Sufficient degradation of the PLGA determined by gel permeation chromatography occurred to release adequate amounts of the GM6001 from the coating within a 7-day period. A cumulative GM6001 release at day 42 was determined to be 77.8±1.4% of the actual GM6001 content within the coating. The coating containing the GM6001 reduced the rate of in vitro cell growth of human aortic smooth muscle cell (HASMC) by 30.7 and 37.4% compared to the metallic substrate only after 4 and 7 days, respectively. However, the MMP-2 activity normalized to cell number was not statistically different between the GM6001 releasing coating and the metal substrate. Using a scrape wound injury assay, the migration of HASMCs was shown to be decreased by 21.4% with GM6001 released from the PLGA coating compared to metallic substrate only. These results suggest that releasing a MMPI from an absorbable coating of a metallic substrate provides a reduction of HASMC proliferation and migration rates, while preserving the overall MMP activity in efforts to retain normal cellular regulation.

A. Vilcinskas et al. disclose in Entomological Research 37 (Suppl. I) (2007) A79 "The greater wax moth *Galleria mellonella* as a mini-host model for human pathogens and as a reservoir of novel peptide antibiotics." The IMPI represents a specific inhibitor of microbial metalloproteinases that are virulence factors of human pathogens. It strongly inhibits prominent thermolysin-like metalloproteinases such aureolysin, bacillolysin, pseudolysin and vibriolysin which have been identified as targets for the development of second generation antibiotics (Clermont et al. 2004). Since thermolysin-like microbial metalloproteinases play well established roles during pathogenesis and cause pathologic Symptoms such as increase of vascular permeability, hemorrhagic edema, and septic injury, the IMPI represents a promising template for the design of novel peptide antibiotics (Wedde et al. 2007).

In summary, most known M4 protease inhibitors were found to exert activity against resistive bacteria only at later stages, whether alone or in combination with antibiotics.

SUMMARY OF THE INVENTION

It is therefore an object of the present invention to provide compound combinations comprising IMPIα or IMPIα-fusion and at least one further bactericidal compound, or nucleic acids encoding for IMPIα or IMPIα-fusions, or their combinations with bactericidal compounds which are efficient in treating bacterial infections, especially infections involving bacteria partially or completely against at least one antibiotic, at any stage of the infection, and especially at early stages. Another aspect of the invention comprises the use of IMPIα or IMPIα-fusion, or nucleic acids encoding for IMPIα or IMPIα-fusions to express these peptides, and optionally at least one further bactericidal compound to treat a bacterial infection, especially infections involving partially or completely resistant bacteria, at any stage of the infection, and especially at an early stage.

The object underlying the invention is accomplished by applying a composition as provided herein. It is understood, that the term "comprising" can be replaced by "consisting of" without adding new matter.

In one embodiment of the invention comprises the composition as components a polypeptide IMPIα (including wild type) and/or a polypeptide IMPIα-fusion and at least one antibiotic compound, in particular an aminoglycoside antibiotic, and/or at least one bactericidal compound, wherein the polypeptides, the at least one antibiotic and/or the at least one bactericidal compound is (are) present in the composition in concentrations which exhibit in combination a synergistic effect against resistant bacteria.

The composition of the invention comprises in another embodiment nucleic acids encoding IMPIα or IMPIα-fusion effective against resistant bacteria, optionally in combination with at least one bactericidal and/or at least one antibiotic compound.

In still another embodiment of the invention the polypeptide is selected from the group consisting of SEQ ID NOs: 10, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, and IMPIα-fusions, having the amino acid sequences of SEQ ID NOs: 6, 8, 12, 86, 88, 90, 92.

Subject matter of the present invention is also a polypeptide suitable in a composition the invention, wherein the polypeptide is selected from the group consisting of SEQ ID NOs: 10, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, and IMPIα-fusions, having the amino acid sequences of SEQ ID NOs: 6, 8, 12, 86, 88, 90, 92.

Subject matter of the present invention is also the use of a polypeptide having at least 70% homology, in particular 80%, 90% or 95% or 100% homology to the polypeptide of SEQ ID No 2 representing the wild-type of the protein insect metalloproteinase inhibitor IMPIα to treat bacterial infection by reducing the bacterial load of a patient as soon as the infection is suspected or diagnosed, or prophylactically before, during, or after surgery, especially to treat bacterial infection caused by bacteria which are at least partially or completely resistant to at least one antibiotic or bactericidal compound.

In an embodiment of the invention the polypeptide is used in combination with a further bactericidal compound, especially at least one antibiotic and/or at least one bactericidal compound, wherein the at least one bactericidal or at least one antibiotic compound is administered in doses lower than inhibitory upon solitary application, or in higher doses up to maximally tolerable doses, and is administered essentially simultaneously to IMPIα or separately in an individual dosing scheme, frequency, and treatment duration, especially with treatment breaks during which IMPIα application is continued.

In a further embodiment of the invention the polypeptide is used for treating bacterial infections which are at least partially caused by bacteria resistant to one or more bactericidal and/or antibiotic compounds.

In yet another embodiment of the invention the polynucleotide coding for the polypeptide of the composition is used to transfect cells of the patient and express said polypeptide in these cells.

In still another embodiment of the invention the polypeptide of the composition can be used for coating or sterilizing devices, especially implants. It can be advantageously be used in combination with other bactericidal compounds.

Subject matter of the present invention is also a pharmaceutical composition containing the polypeptide of the composition the invention suitable for injection, inhalation or topical application.

In one embodiment of the pharmaceutical composition it can comprise further at least one bactericidal and/or at least one antibiotic compound.

Subject matter of the invention is also the composition of the invention for use in the treatment of an infection of a patient caused by bacteria resistant against one or more antibiotic and/or bactericidal compound, in particular for use in the early treatment of an infection caused by bacteria resistant against one or more antibiotic and/or bactericidal compound.

As used herein, the following terms have the following meanings unless expressly stated to the contrary.

The term "device" comprises device used in a clinical setting and especially devices being in contact with patients, and in particular devices being temporarily or permanently in contact with body fluids like blood, serum, lymph, etc., which will be transferred back into the body, or implants designated to be positioned inside a patient's body. Devices comprise stents, cathetres, intraveneous cannulae, pace makers, artificial joints and bones, biodegradable and permanent medication deposits, patches and debridements, and dental fills and crowns.

The term "patient" comprises humans infected by bacteria or prone to bacterial infection, regardless of their gender, age, genomic profile, ethnic or anamnesis. It also includes all animals infected by bacteria, escpecially domestic animals, such as farm animals including birds and fish, and companion animals like dogs and cats.

The term "wtIMPIα" refers to a protein with an amino acid sequence as in SEQ ID NO:2 and consists of the N-terminal fragment of the full length IMPI molecule which is endogenously cleaved from the larger precursor molecule IMPI.

The term "mtIMPIα" or "Mutein IMPIα" comprises all recombinant or synthetic proteins with an amino acid sequence which is at least 70%, especially 80% 90%, 95% homologous, but not identical to SEQ ID NO: 2 (wtIMPIα) and which inhibits at least one protease of the M4 protease family with an $IC_{50}$<1000 nM, especially $IC_{50}$<100 nM, including those solely mutated in the amino acid stretch 35 to 39, such as those listed in amino acid sequence SEQ ID NO: 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84.

The term "M4 protease" refers to the definition given in the MEROPS online database of peptidases (http://merops.sanger.ac.uk/cgi-bin/famsum?family=M4).

The term "biologically active" as used herein refers to wtIMPIα or mtIMPIα demonstrating inhibition of thermolysin or another member of the M4 protease family with an $IC_{50}$<1000 nM especially $IC_{50}$<100 nM or about 10 nM.

The term "IMPIα" shall include biologically active mtIMPIα and wtIMPIα, which may be chemically modified.

The term "IMPIα-fusion" shall include biologically active IMPIα being part of a larger peptide or protein The term "resistant bacteria" refers to some subpopulations of bacterial species, which are able to survive after exposure to one or more antibiotics or bactericidial compounds. Bacteria resistant to multiple antibiotics or bactericidial compounds are considered multidrug resistant (MDR).

The term "early stage" of an infection means at diagnosis of an infection, before diagnosis when only unspecific symptoms of infections are manifest, or even prophylactic, i.e. when a risk of infection is assumed, and no symptoms are manifest. At early stages of an infection bacteria are still in low concentrations at exponential or log growth phases and have not yet formed biofilms to a large extent. A treatment applied at early stage of infections is called an early tetreatment.

The term "antibiotic compound" means an agent that either kills or inhibits the growth of a microorganism.

In particular the antibiotic compound is an aminoglycoside antibiotic, e. g.

| Generic | Brandname |
| --- | --- |
| Amikacin | Amikin |
| Gentamicin | Garamycin, G-Mycin, Jenamicin |
| Kanamycin | Kantrex |
| Neomycin | Mycifradin, Myciguent |
| Netilmicin | Netromycin |
| Paromomycin | |
| Streptomycin | |
| Tobramycin | Nebcin |

The term "bactericidial compounds" means a substance that kills bacteria. Bactericides are e.g. disinfectants, antiseptics, or antibiotics.

The term "synergistic" means that the interaction of multiple elements in a system producing an effect different from or greater than the sum of their individual effects.

BRIEF DESCRIPTION THE DRAWINGS

FIG. 1: Comparison of growth curves of *P. aeruginosa* cultures (DSM No. 50071) in the presence (long dashed line)

and absence (short dashed line) of the M4-metalloprotease inhibitor IMPIα (45 μM; NB-Medium No. 5) in presence of (a) 1.000, (b) 500, (c) 250 and (d) 125 ng/ml Gentamycin.

Figure 2A:
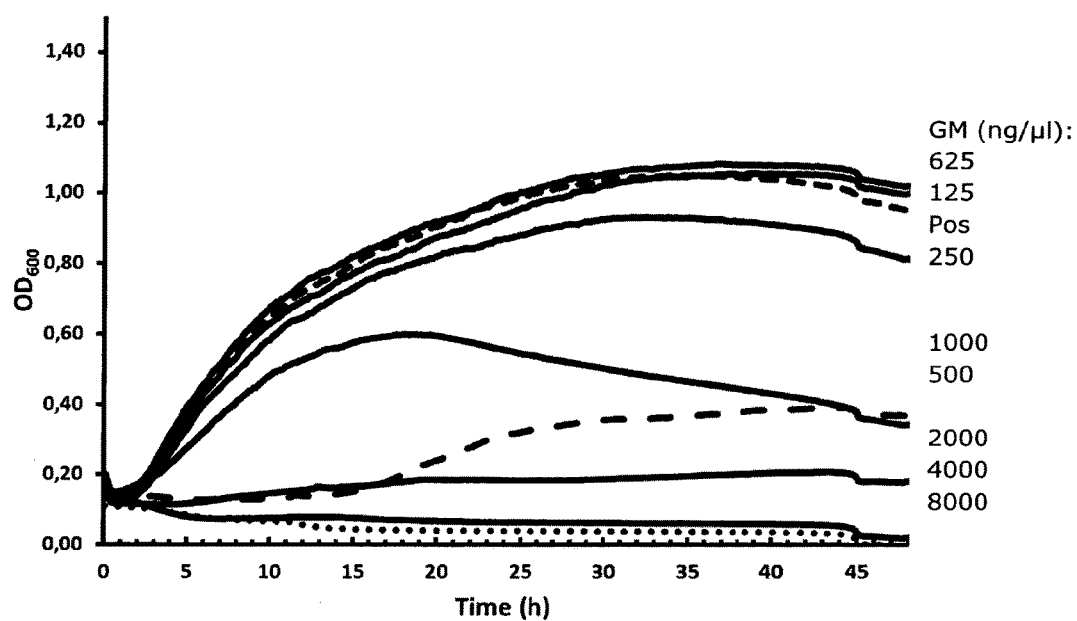
Figure 2B:
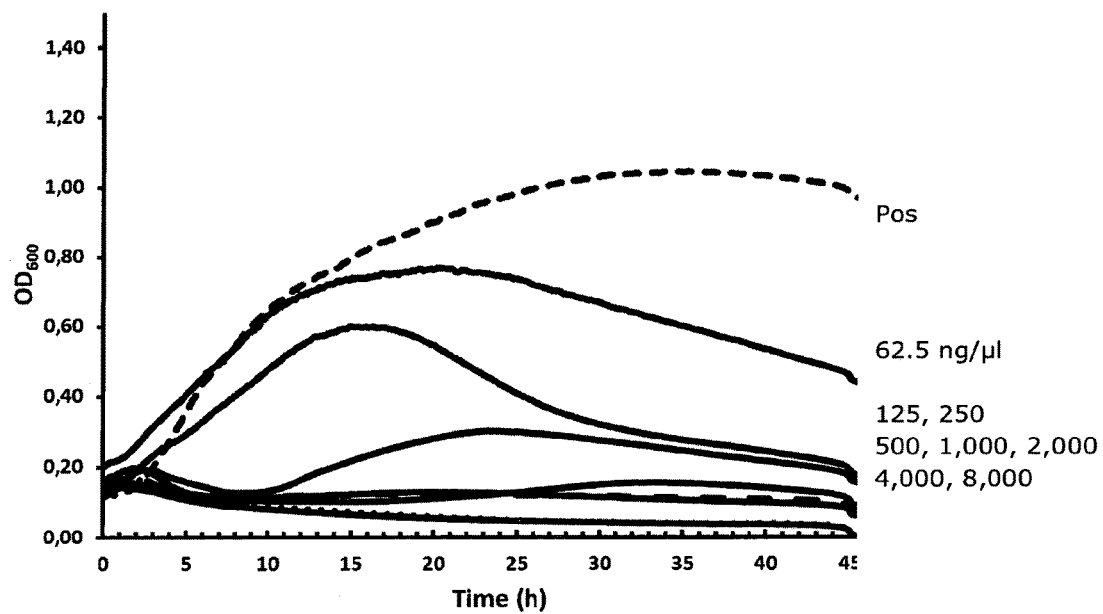
Figure 3A:
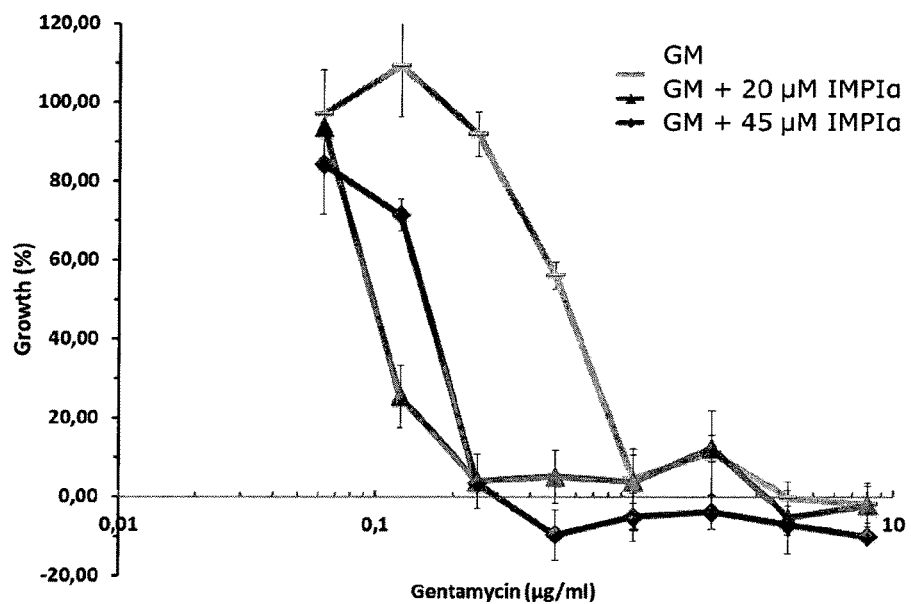
Figure 3B:
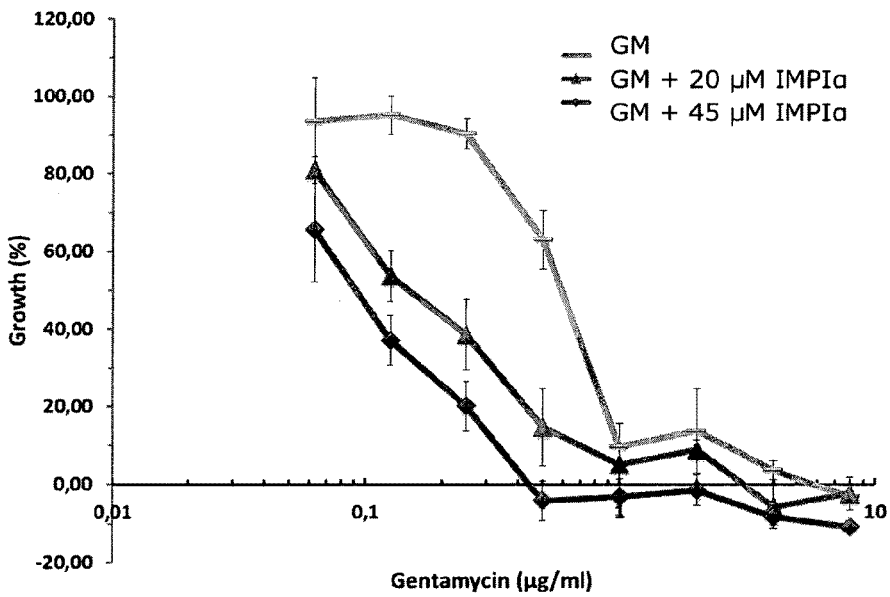
Figure 3C:
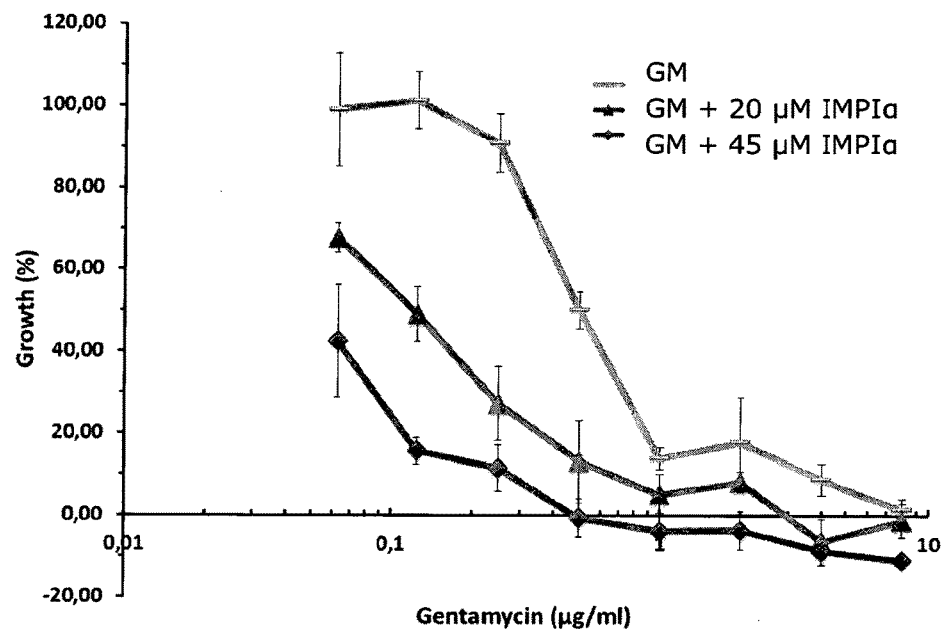
Figure 3D:
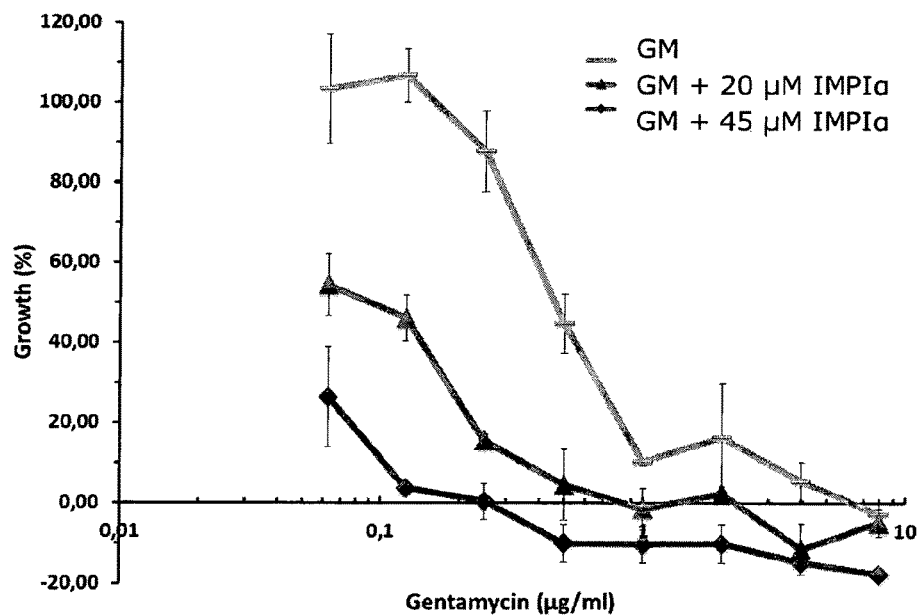

FIG. 2: Growth curves of *P. aeruginosa* cultures (DSM No. 50071) in presence of different Gentamycin concentrations (8,000; 4,000; 2,000; 1,000; 500; 250; 125; 62.5 ng/ml; NB-Medium) (a) without and (b) in presence of M4-metalloprotease inhibitor IMPIα (45 μM; NB-Medium No. 5)

FIG. 3: Growth curves of *P. aeruginosa* cultures (DSM No. 50071) in presence of 45 (black, diamond symbols) and 20 (dark grey, triangles) μM IMPIα and absence (light grey, horizontal bars) of IMPIα (NB-Medium No. 5), in presence of different gentamycin concentrations (8000; 4000; 2000; 1000; 500; 250; 125; 62.5 ng/ml) (a) after 12 h (b) after 24 h (c) after 36 h and (d) after 48 h.

Figure 4:
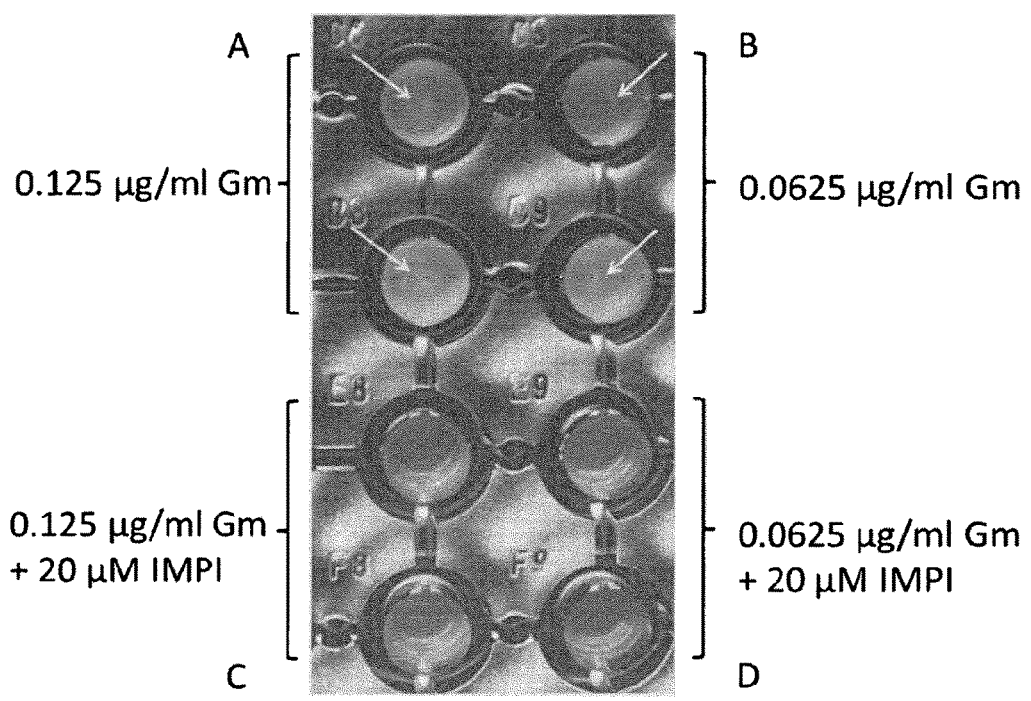

FIG. 4: The formation of freely suspended biofilm in flocs is a successful strategy used by *Pseudomonas aeruginosa* to overcome stressfull envionmental conditions (e.g. addition of Gentamicin Gm to buffer; Panel A (62.5 ng/ml) and B (125 ng/ml)). When incubated with Insect Metalloprotease Inhibitor (IMPIα), biofilm formation is prohibited (Panel C and D at 62.5 and 125 ng/ml Gm doses, respectively).

Figure 5A:
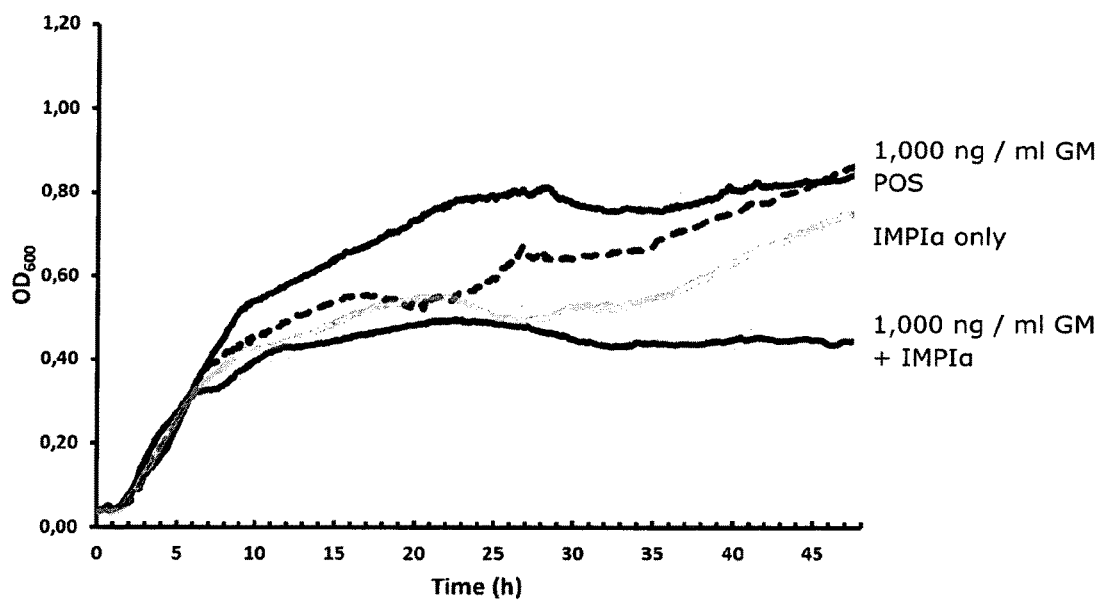
Figure 5B:
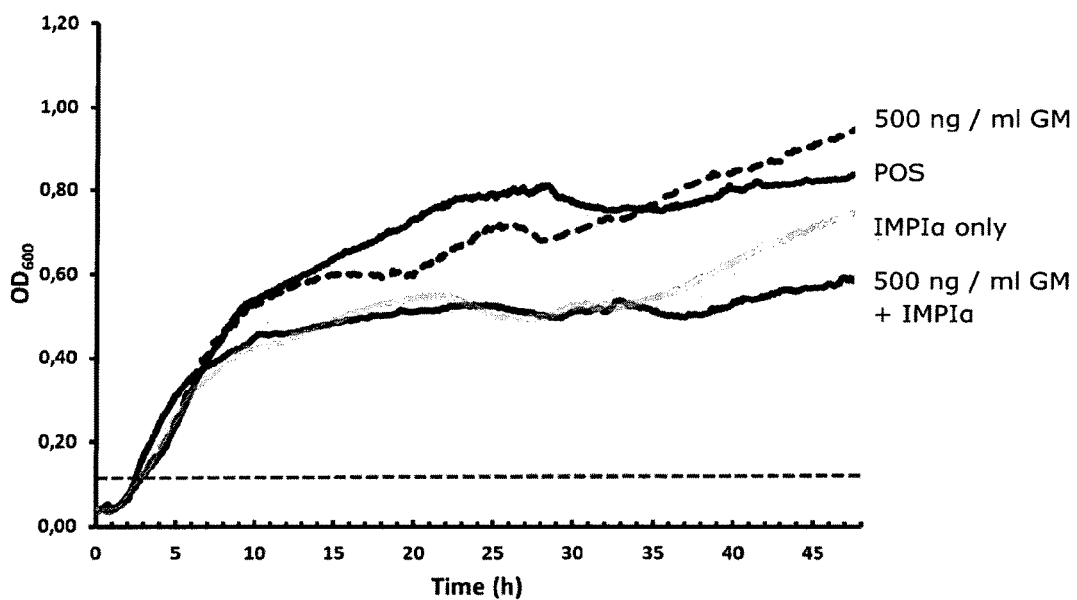
Figure 5C:
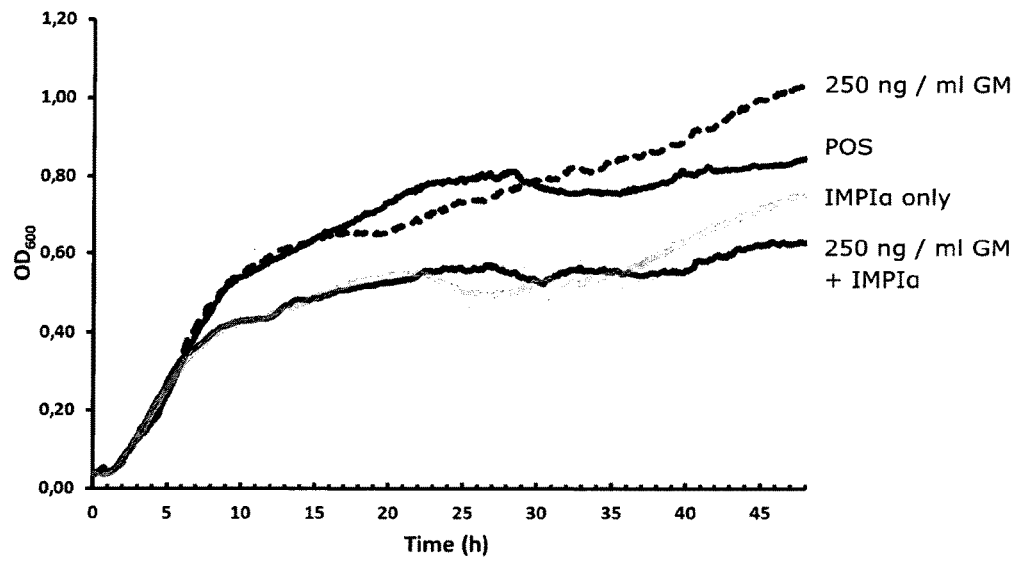
Figure 6:
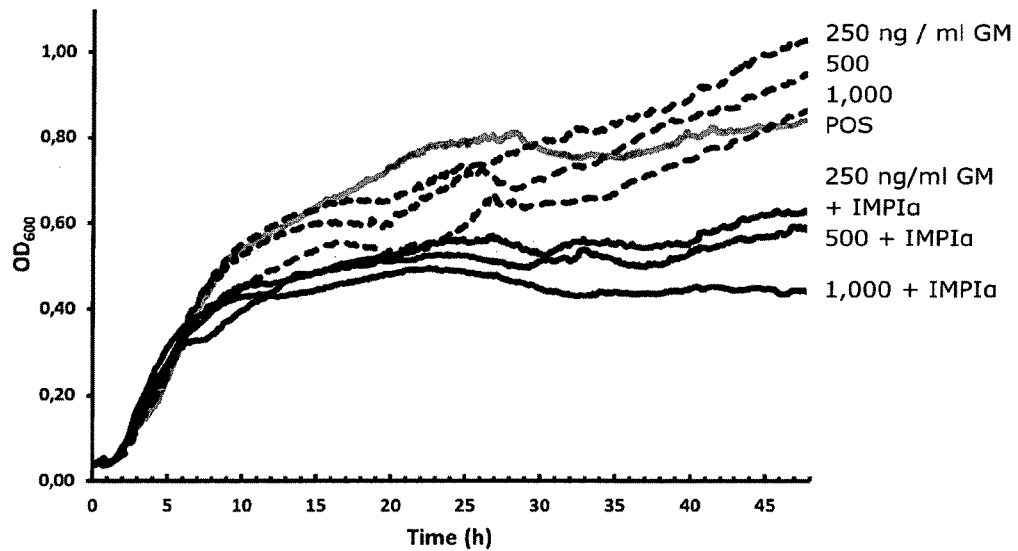

FIG. 5: Comparison of growth curves of *P. aeruginosa* cultures (VB7623, Cllinical isolate from tracheal secrete) in presence (long dashed line) and absence (short dashed line) of the M4-metalloprotease inhibitor IMPIα (25 μM; NB-Medium No. 5) in presence of (a) 1,000 (b) 500, and (c) 250 ng/ml Gentamycin FIG. 6: At low concentrations of gentamycin (dashed lines) the growth rate of *P. aeruginosa* cultures VB7623 seem to enhance growth after 26 h in NB-medium, a growth which could be part of general stress response.

Figure 7:
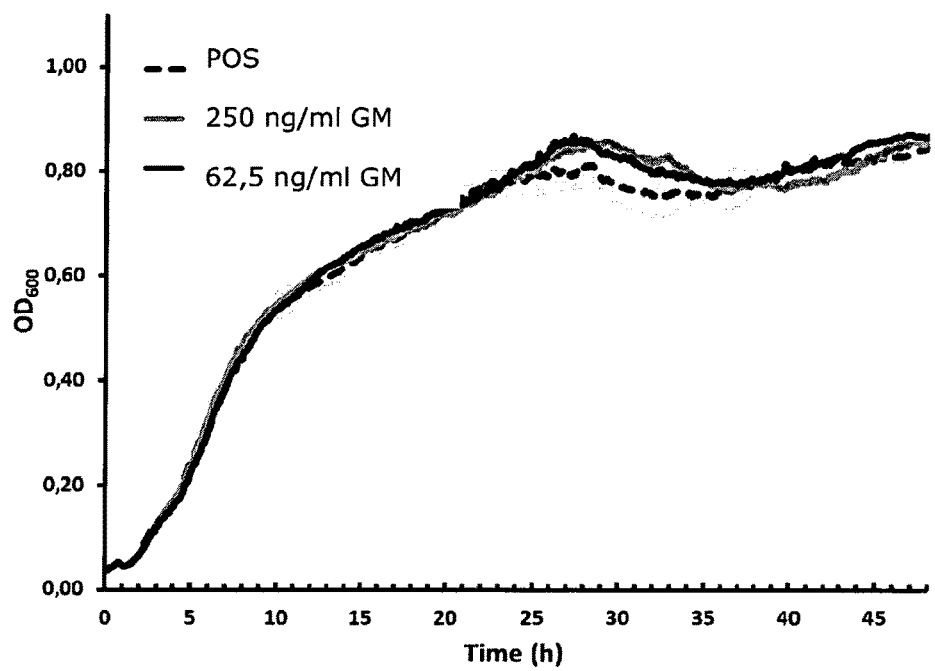
Figure 8A:
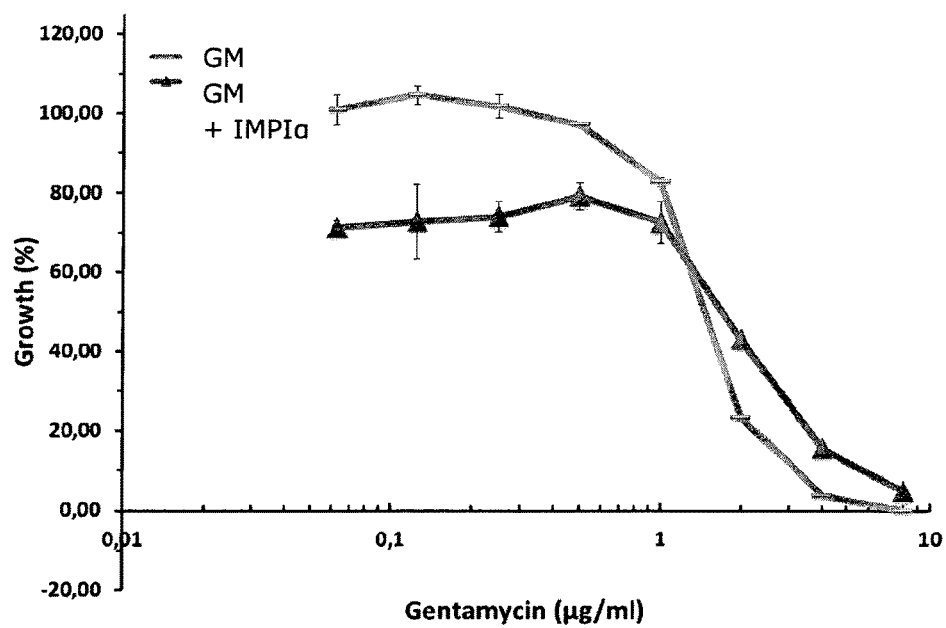
Figure 8B:
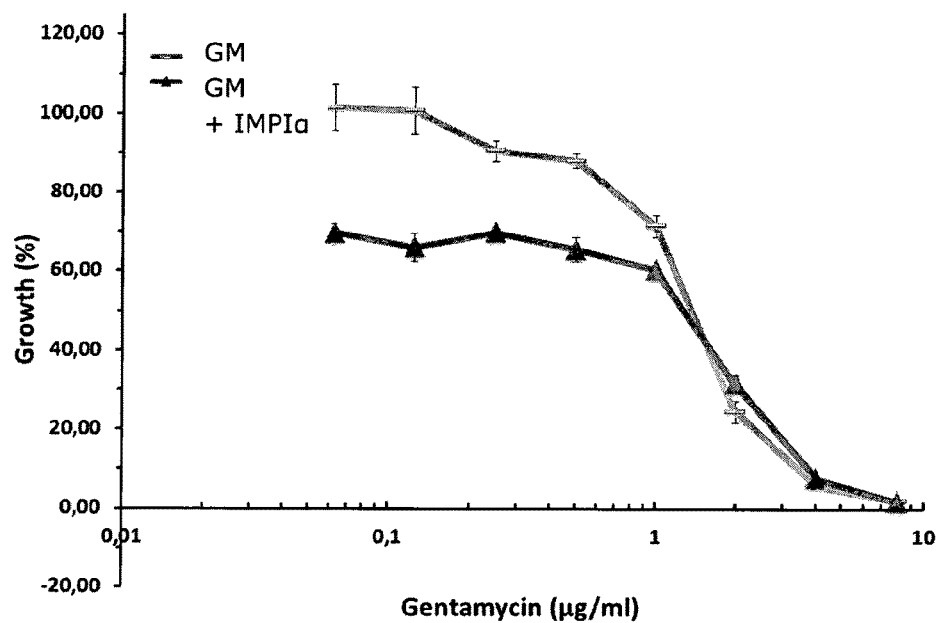
Figure 8C:
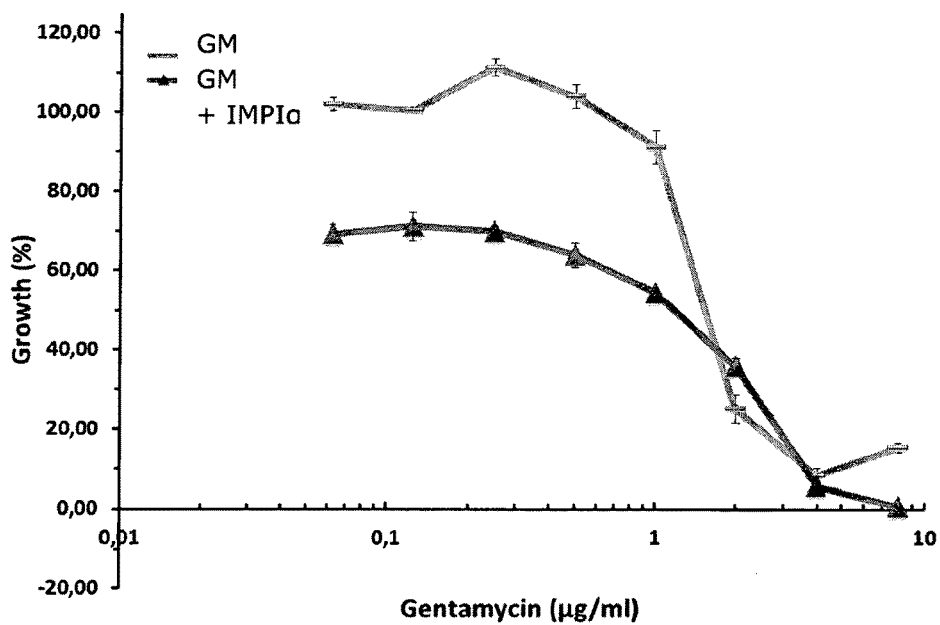
Figure 8D:
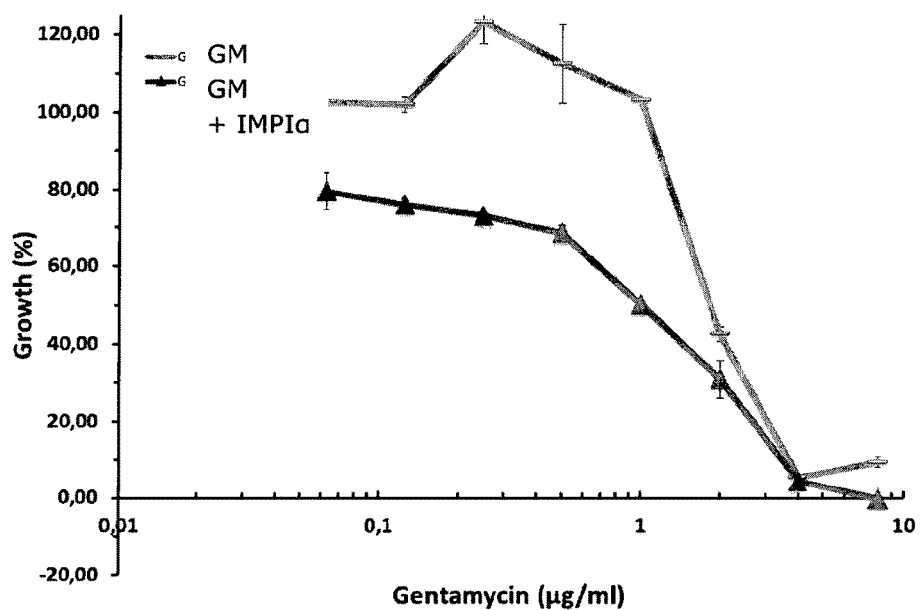

FIG. 7: At very low concentrations gentamycin has no effect on the growth rate of *P. aeruginosa* cultures VB7623. Furthermore no stress response can be observed.

FIG. 8: Growth curves of *Pseudomonas aeruginosa* cultures (Clinical Isolate VB7623 from tracheal secrete, assessed as 4MRGN strain [EUCAST]) in presence (dark grey, triangles) and absence (light grey, horizontal bars) of the M4-metalloprotease inhibitor IMPIα (25 μM, NB-Medium No. 5) in presence of different gentamycin concentrations (8000; 4000; 2000; 1000; 500, 250, 125, 62.5 ng/ml) (a) after 12 h (b) after 24 h (c) after 36 h and (d) after 48 h.

Figure 9:
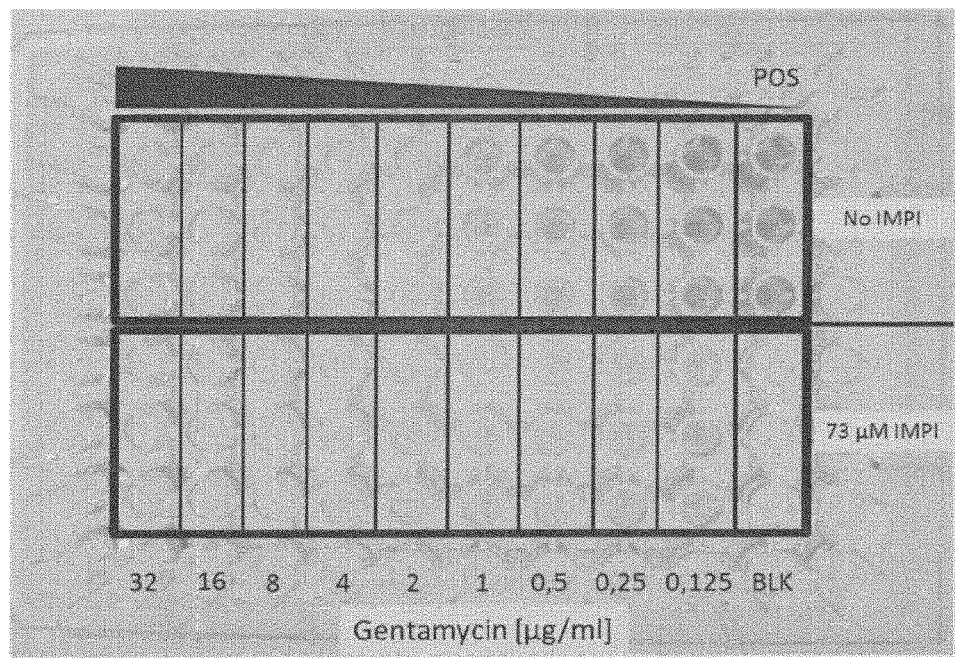

FIG. 9: Comparison of the development of pyoveridine (dark grey background in circular light grey structure, i.e. the plate wells) during growth of *P. aeruginosa* (Clinical Isolate VB7623 from tracheal secrete, assessed as 4MRGN strain [EUCAST]) in presence (lower rectangle) and absence (upper rectangle) of the M4-metalloprotease inhibitor IMPIα (73 μM; NB-Medium No. 5), and different Gentamycin concentrations (32; 8; 4; 2; 1; 0.5; 0.25; 0.125 μg/ml) in a 96-well plate after 48 h. Pyoveridine is not expressed in the concurrent presence of IMPI and Gentamycin, not even at gentamycin concentrations as low as 0.125 μg/

Figure 10:
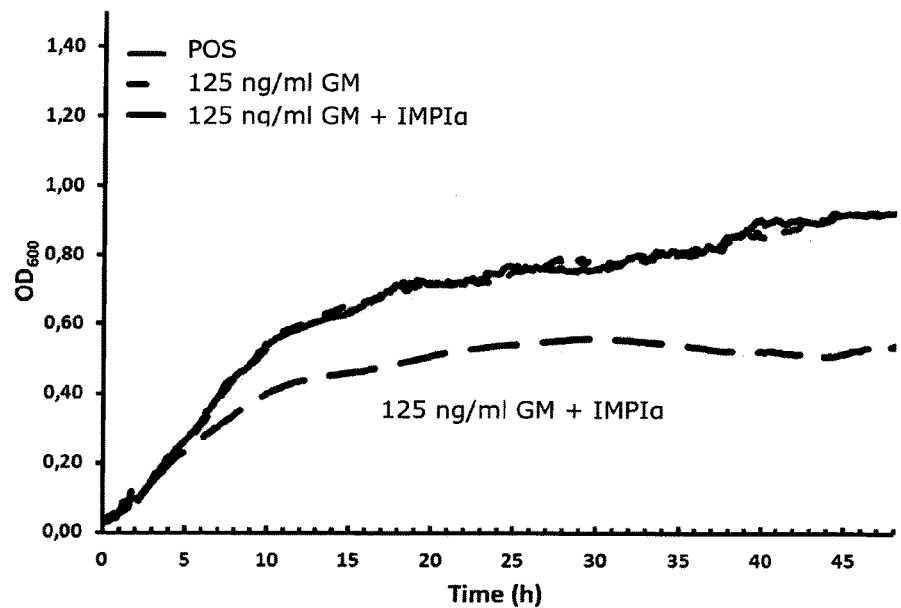

FIG. 10: Comparison of growth curves of *P. aeruginosa* *P. aeruginosa* cultures (VB7623, Clinical isolate from tracheal secrete) in the presence (long dashed line) and absence (short dashed line) of the M4-metalloprotease inhibitor IMPIα (73 μM; NB-Medium No. 5) in presence of 125 ng/ml gentamycin.

Figure 11:
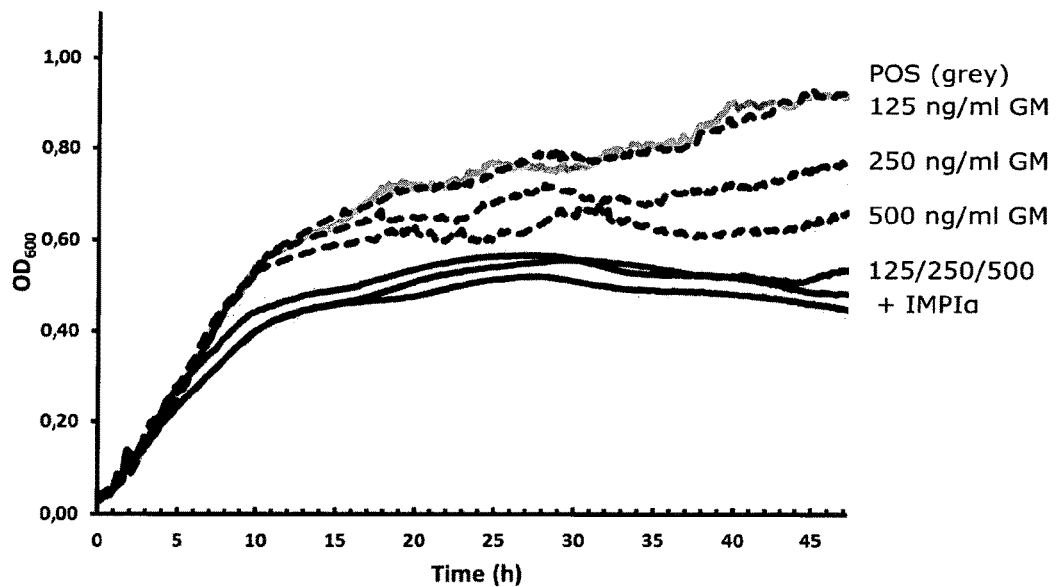
Figure 12A:
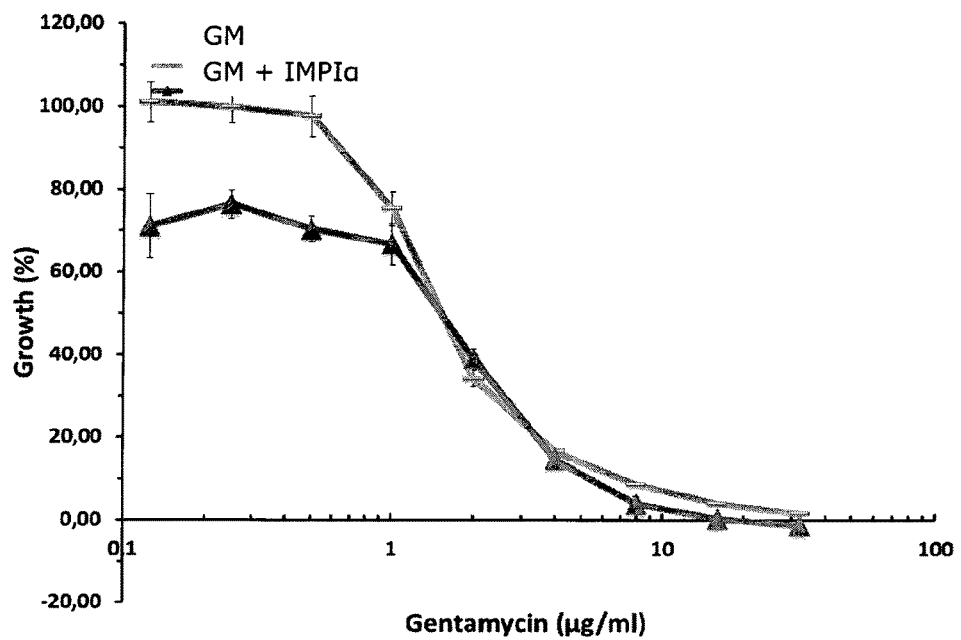
Figure 12B:
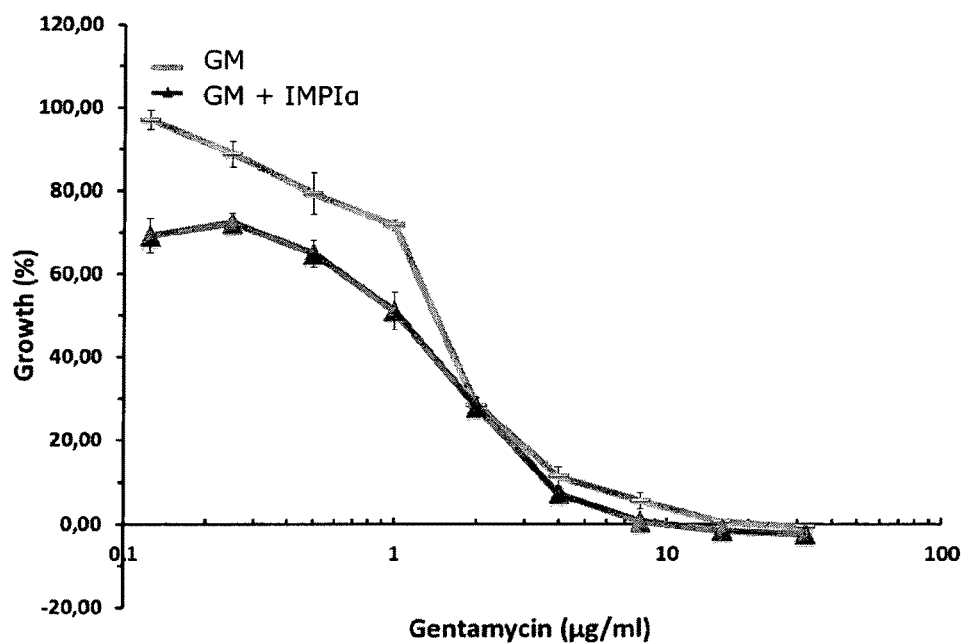
Figure 12C:
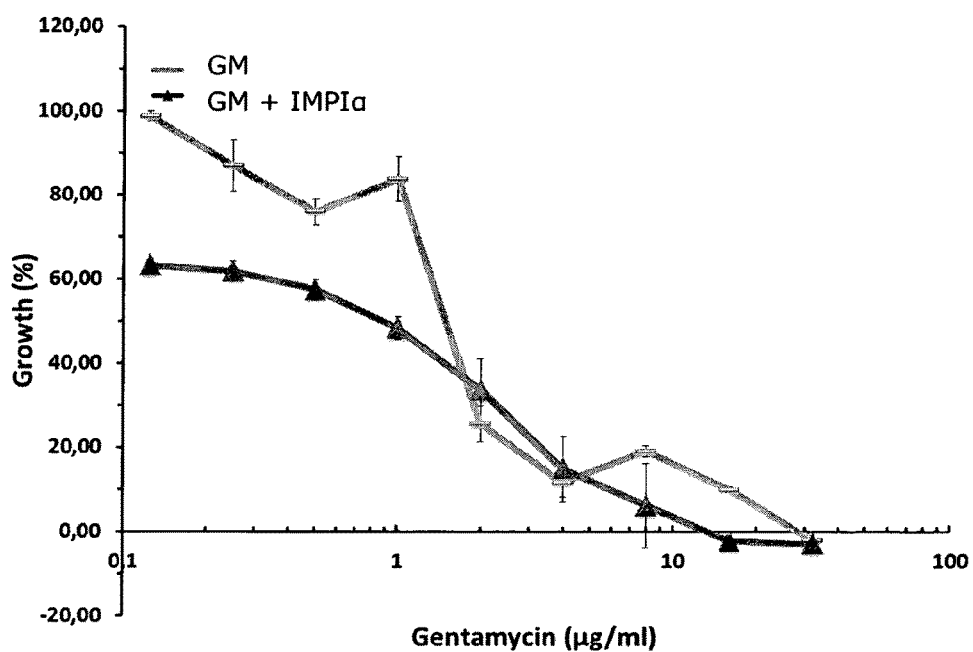
Figure 12D:
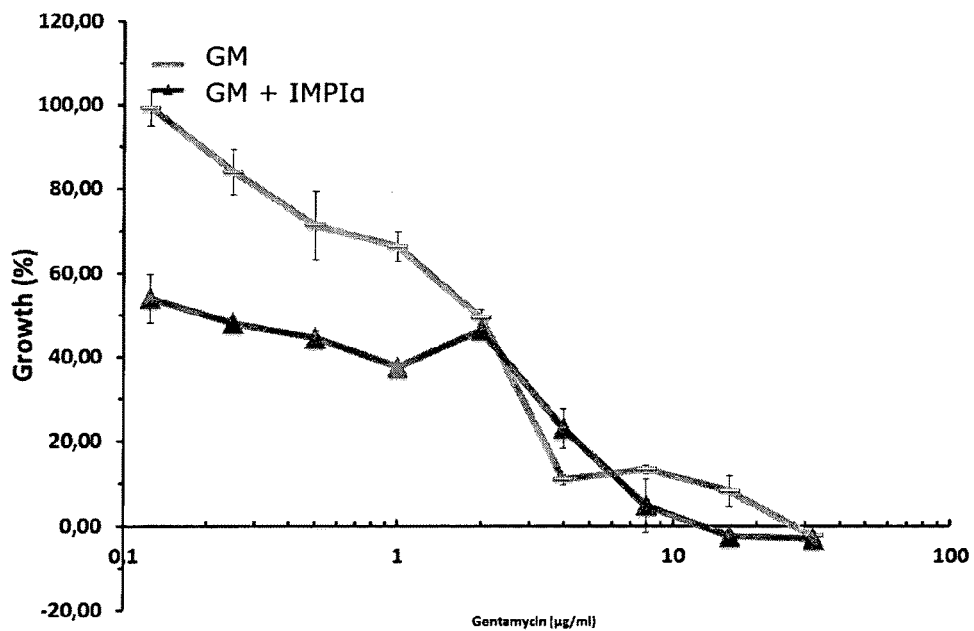

FIG. 11: Comparison of growth curves of *P. aeruginosa* cultures (VB7623, Clinical isolate from tracheal secrete) in presence (dark thick line) and absence (short dashed line) of the M4-metalloprotease inhibitor IMPIα (73 μM; NB-Medium No. 5) in presence of different gentamycin-concentrations (500; 250; 125 ng/ml GM), positive control in grey.

FIG. 12: Comparison of growth curves of *P. aeruginosa* cultures (clinical isolate VB7623 from tracheal secrete, assessed as 4MRGN strain [EUCAST]) in the presence (dark grey) and absence (light grey) of the M4-metalloprotease inhibitor IMPI (73 μM; NB-Medium No. 5). in the presence of different Gentamycin concentrations (32; 8; 4; 2; 1 μg/ml; 500; 250; 125; 62.5 ng/ml) after (a) 12 h, (b) 24 h, (c) 36 h, (d) 48 h.

FIG. 13: Antibiogram of the *Pseudomonas aeruginosa* strain VB7623 which was isolated from the tracheal secrete of a patient. The strain was assessed as multiresistant Gram-negative strain (4MRGN [EUCAST]).

Figure 14B:
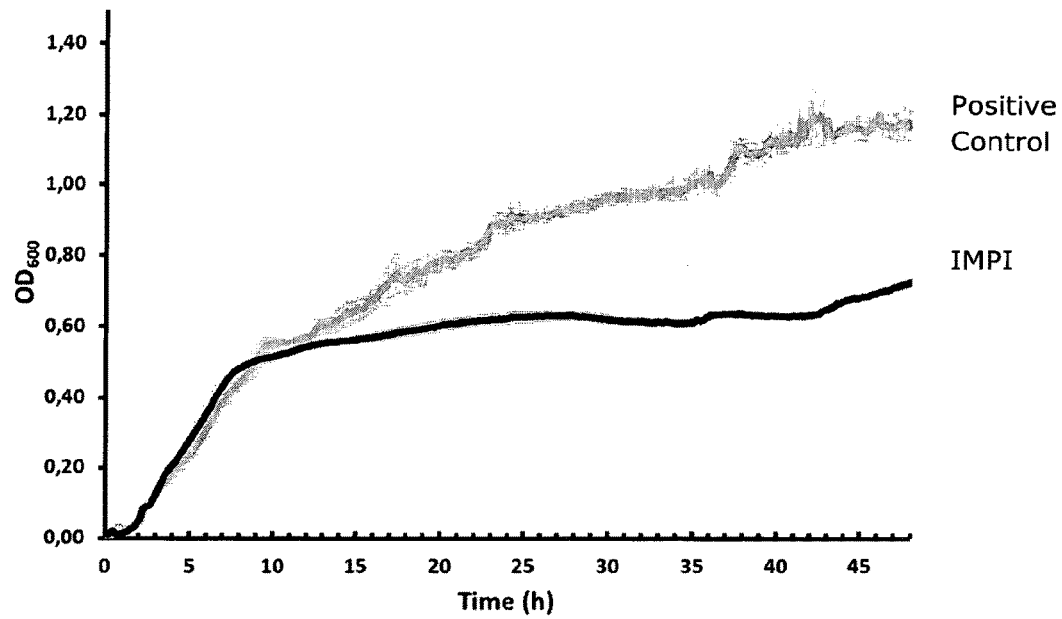

FIG. 14: Comparison of growth curves of *P. aeruginosa* cultures (VB7623, clinical isolate from tracheal secrete) in the presence (black line) and absence (grey line) of the M4-metalloprotease inhibitor IMPIα without the use of gentamicin or any other antibiotics. IMPIα concentration is (a) 25 μM; NB-Medium No. 5 and (b) 60 μM; NB-Medium No. 5.

Figure 15:
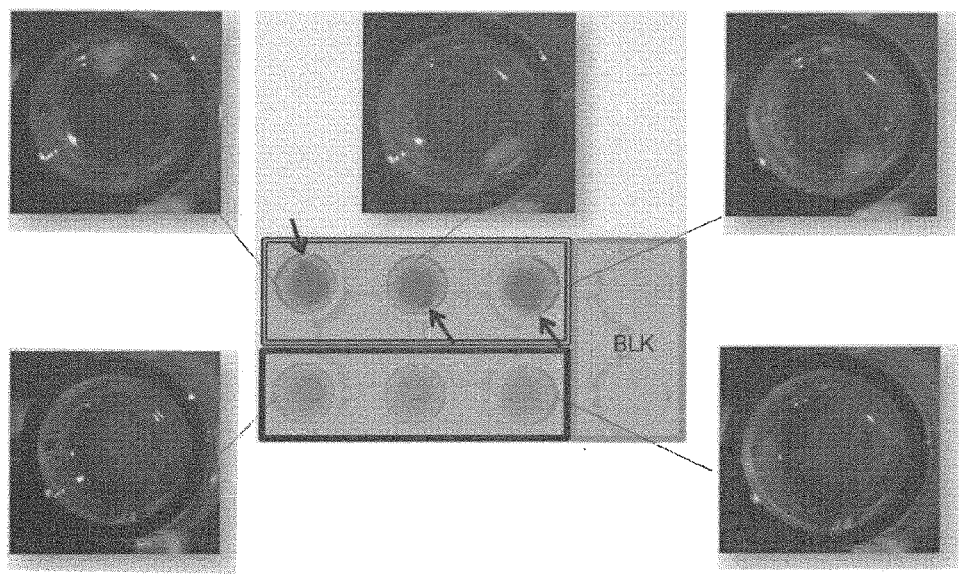

FIG. 15: Comparison of the development of planctonic biofilm and pyoveridine (grey colour in the wells) during growth of *P. aeruginosa* (clinical isolate VB7623 from tracheal secrete, assessed as 4MRGN strain [EUCAST]) in the presence (black outlined rectangle) and absence (double outlined rectangle) of the M4-metalloprotease inhibitor IMPI (60 μM; NB-Medium No. 5) in a 96-well plate after 48 h. Pyoveridine (grey colour) is secreted less in presence of IMPIα, in which case also no plantonic biofilm can be observed.

Figure 16A:
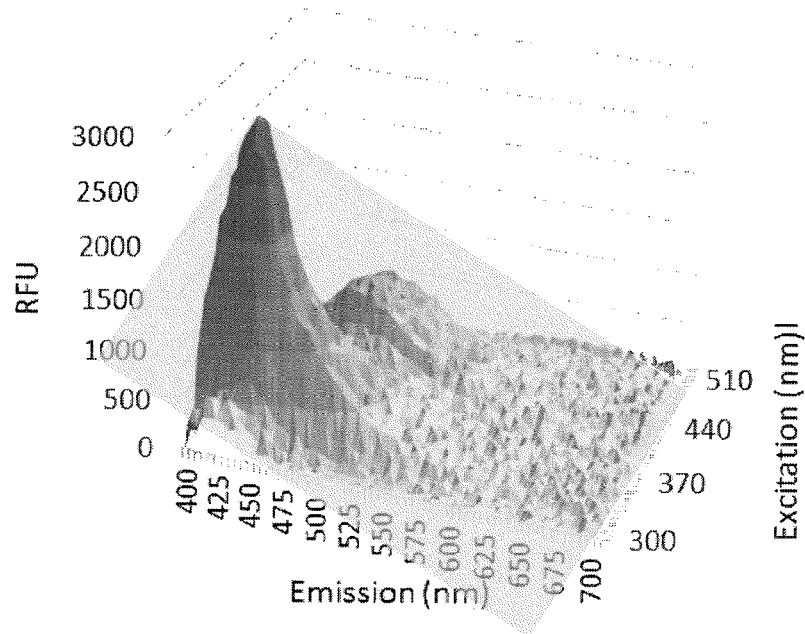
Figure 16B:
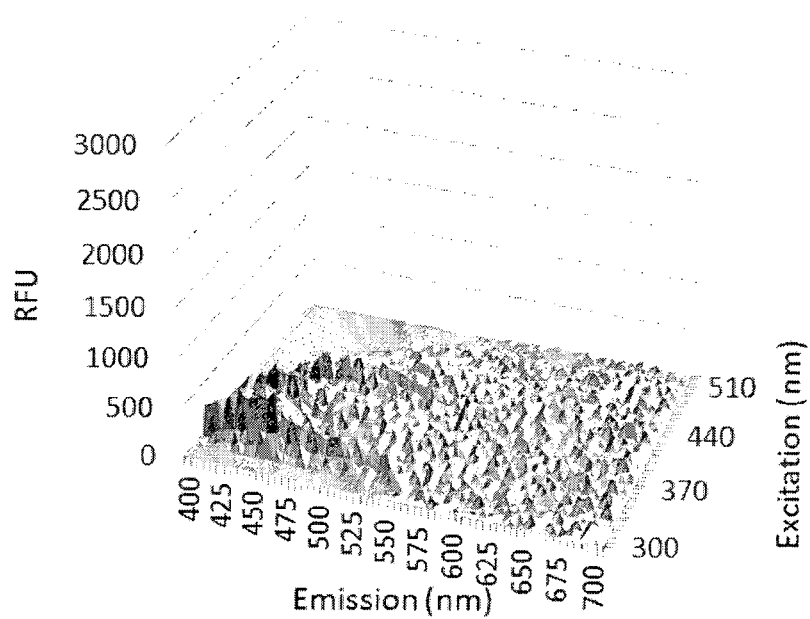

FIG. 16: Excitation and emission scan of the fluorophores (a) pyochelin and (b) pyoveridin. Both molecules are essential for virulence and are expressed upon quorum sensing. A difference spectrum was taken by centrifuging the cultivation medium and measuring the supernatant against medium.

DETAILED DESCRIPTION OF THE INVENTION

The inventors discovered that applying IMPIα, having for example the amino acid sequences of SEQ ID NOs: 10, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, and IMPIα-fusions, having for example the amino acid sequences of SEQ ID NOs: 6, 8, 12, 86, 88, 90, 92, reduce and stop growth of resistant bacteria at any stage of the infection, especially when applied in combination with at least one further bactericidal compound, surprisingly when the composition of the invention was applied at early stages of the infection. This observation is surprising because IMPIα interfere with M4 protease activity, for example with thermolysin, pseudolysin, aureolysin, vibriolysin, bacillolysin and npr599, which are shed only at high bacterial concentrations, e.g. during or after biofilm formation as is the case for *pseudomonas aeruginosa*. Therefore one has to expect that M4 protease inhibitors only interfere with bacteria after biofilm growth, as several publications on non resistant bacteria suggest.

The inventors discovered, however, that IMPIα and IMPIα fusions or its combination with bactericidal compounds delays, stops or even reverses growth of resistant bacteria in a solution containing just non adherent bacteria. In this experiment, care was taken by visual inspection that biofilm formation and hence protease shedding had not yet started. More precisely it was observed that a delay of bacterial growth starts much earlier during the so called "late log" (late logarithmic) phase, when bacterial growth kinetics still follows a logarithmic function of time.

The inventors also discovered that IMPIα and IMPIα fusions or its combination with at least one bactericidal compound effectively prohibits biofilm formation, even for resistant bacterial strains.

Furthermore the inventors discovered that combining IMPIα or IMPIα-fusions and antibiotics always inhibits growth of resistant bacteria synergistically, regardless of the antibiotics concentration and the stage of the infections. Even at sub inhibitory antibiotic doses IMPIα or IMPIα-fusions interfere with bacterial growth.

The inventors observed, for example, that the synthesis of the P. aeruginosa siderophore pyoverdine, known to be involved in the synthesis of virulence factors, is inhibited synergistically by IMPIα and the antibiotic gentamycin.

Thus, subject matter of the invention are compositions containing IMPIα or IMPIα-fusions and at least one further bactericidal compound, and the use of any IMPIα against partially or completely resistant or even multiresistant strains of bacteria, such as multiresistant *Staphylococcus aureus* (MRSA) alone or in combination with antibiotics or other bactericidal compounds to treat patients or protect devices, especially implants. This use of IMPIα or IMPIα-fusions is particularly advantageous since it is bactericidal even without applying antibiotics in parallel, or even with very low doses of antibiotics. IMPIα or IMPIα-fusions may be used to affect bacteria being planktonic, isolated sessile or forming biofilms, at any stage of an infection including early stages. Thus, bacteria resistant against antibiotics will still be affected by IMPIα. Moreover, IMPIα can act synergistically with antibiotics in areas of the patient's body where antibiotics concentrations are low due to, e.g., rapid dilution or low drug influx related to low diffusion rate or mechanisms inducing active outflow of the drug. So by use of IMPIα and IMPIα fusions and combinations with bactericidal compounds according to the invention these areas cannot become areas where, due to sub inhibitory concentrations of the antibiotic, bacteria could respond to the challenge by developing resistance.

Further contemplated is the use of IMPIα or IMPIα-fusions with the IMPIα element exhibiting additional modifications, such as chemical modifications in the side chain or at the N and/or C terminal for improving biological or chemical properties such as bioavailability, stability, and effectivity. The modification may also provide for a detectable label, for example a chemiluminescent structural element, one or more radioactive isotopes in one or more side chains of an amino acid in the polypeptide, an enzyme which is able to generate a colour reaction and the like. A cystein, for example, may be added for linking a water soluble polymer such as polyethylene glycol, or other amino acids like lysine, cysteine, histidine, arginine, asparaginic acid, glutamic acid, serine, threonine, or tyrosin could also be used for coupling polymers to the peptide. Another example is the insertion of tripeptide sequences NXT or NXS or fragments thereof with X designating any amino acid except P, which may be recognized by a cellular enzyme adding glycosylation elements. Suitable, clinically acceptable, water soluble polymers include polyethylenglycol (PEG) and polysialic acid (PSA).

IMPIα-fusions according to the invention comprise IMPIα and at least one polypeptide having a physiological function, in particular IMPIR, an antibody or antibody fragment, scaffolds such as lipocalin, ankyrin, fibronectin, transferrin, tetranectin, adnectin, albumin, uteroglobin, or protein A, functional peptides such as transferrin, peptides useful for diagnostic applications, such as green fluorescent protein (GFP), or peptide tags enabling immobilization on technical surfaces, such as hexahistidine, or glutathione-S-transferase (GST).

There are three super families (cytosolic, mitochondrial, and MAPEG) of GSTs: while classes from the cytosolic super family of GSTs possess more than 40% sequence homology, those from other classes may have less than 25%. Cytosolic GSTs are divided into 13 classes based upon their structure: alpha, beta, delta, epsilon, zeta, theta, mu, nu, pi, sigma, tau, phi, and omega. Mitochondrial GSTs are in class kappa. The MAPEG super family of microsomal GSTs consists of subgroups designated I-IV, between which amino acid sequences share less than 20% identity. Human cytosolic GSTs belong to the alpha, zeta, theta, mu, pi, sigma, and omega classes, while six isozymes belonging to classes I, II, and IV of the MAPEG super family are known to exist:

| GST Class | *Homo sapiens* GST Class Members |
| --- | --- |
| Alpha | GSTA1, GSTA2, GSTA3, GSTA4, GSTA5 |
| Kappa | GSTK1 |
| Mu | GSTM1, GSTM1L (RNAi), GSTM2, GSTM3, GSTM4, GSTM5 |
| Omega | GSTO1, GSTO2 |
| Pi | GSTP1 |
| Theta | GSTT1, GSTT2, GSTT4 |
| Zeta | GSTZ1 (aka GSTZ1 MAAI-Maleylacetoacetate isomerase) |
| Microsomal | MGST1, MGST2, MGST3 |

An IMPIα fusion may also comprise a linker of 1-100 amino acids between IMPIα and the polypeptide.

Another subject matter of the invention are nucleic acids, especially single stranded RNA, coding for IMPIα or IMPIα-fusion, which are administered into a patient and taken up by cells into their cytoplasm, where the cellular protein expression machinery expresses the IMPIα or IMPIα-fusion from the nucleic template. Preferred are nucleic acids coding for an IMPIα-fusion, wherein the fused element comprises a signal peptide inducing secretion of the assembled and posttranslationally modified IMPIα-fusion protein. Once secreted, the IMPIα-fusion protein acts in a manner similar to an IMPIα or IMPIα-fusion protein directly applied to the patient.

Nucleic acids according to the invention may be modified to resist degradation and improve delivery. Useful modifications include LNA (Locked nucleic acids) or PNA (peptide nucleic acids), and phosphodiester or phosphorothioate modified backbones. Specific formulations for nucleic acid administration in a pharmaceutical composition include liposomes.

The use of the polypeptide or fusion polypeptide comprising IMPIα according to the invention includes treating patients, such as humans or animals infected by microorganisms capable of secreting bacterial toxins of the M4 or Metzincin family of metalloproteinases, in particular thermolysine, aureolysin, bacillolysin, pseudolysin, vibriolysin, Msp peptidase, Mpl Peptidase, or anthrax npr599.

In another aspect of the invention, the simultaneous use of antibiotics or other bactericidal compounds, and IMPIα or IMPIα-fusions is provided at any time of infection, including early stages. Simultaneous application may comprise dosing schemes with a delay between application of antibiotics and M4 protease inhibitors, a different application frequency or different and individually evolving dosings.

These drug application schemes may prove beneficial for the patient or facilitate the application.

Bactericidal compounds amenable for use according to the invention include all antibiotics, such as listed in http://en.wikipedia.org/wiki/List_of_antibiotics, for example. They further include antibodies like the anti-*Pseudomonas*-PcrV antibody Fab' fragment (KB001, Kalos Therapeutics, Inc.), and a fully human IgG1 antibody highly specific for *S. aureus* Exotoxin (KBSA 301, Kenta Biotech Ltd.)

Subject matter of the invention are also the use of IMPIα or IMPIα fusions or a nucleic acid comprising a section coding for IMPIα or IMPIα-fusions in a suitable pharmaceutical composition and the use thereof to treat bacterial infections, especially in combination with antibiotics in a single pharmaceutical composition so that they are always applied simultaneously to the patient.

Another embodiment of the invention comprises the use of antibiotics or other bactericidal compounds in one pharmaceutical composition and of IMPIα or IMPIα-fusions or a nucleic acid comprising a section coding for IMPI or IMPIα or IMPIα-fusions in a separate one. The separate entities can be advantageous for treating patients since the doses relative to each other can be varied independently over time, as well as the individual frequency of administration. A delayed application of the two compositions may be beneficial to prohibit side effects to occur or to limit their strength. Separate entities exhibit the further advantage that different formulations can be chosen, which may even be required for particular molecule combinations.

Subject matter of the invention are also particular dosing schemes, such as combining maximum doses for both, IMPIα and bactericidal compounds. Another dosing scheme may include reduction of the applied dose of the bactericidal compound for some time, even down to sub inhibitory doses, where the combination of IMPIα and the bactericidal compound is still active. The benefit of such temporary dose regimen would be to encounter development of resistance against the compounds.

IMPIα or IMPIα-fusions may be combined with ingredients to form a pharmaceutical composition. The pharmaceutical composition may include water and salts at physiological concentrations, solubilizing or dispersing agents, or anti-oxidant, or particles forming micelles, such as liposomes. This pharmaceutical composition may be filled in a glass or plastic vials, or in a syringe. The pharmaceutical composition may also contain additives supporting drying or freeze-drying of the pharmaceutical composition, for example cyclodextrins or saccharides, in particular disaccharides.

IMPIα or IMPIα-fusions or nucleic acids encoding for IMPIα or IMPIα-fusions and combinations with bactericidal compounds may be administered parenterally, orally, or topically using suitable pharmaceutical compositions, or attached to a patch or wound debridement from where the medication elutes into a wound of the patient.

IMPIα or IMPIα-fusions or nucleic acids encoding for IMPIα or IMPIα-fusions and combinations with bactericidal compounds may be administered in biodegradable containers suitable for implantation into patients, or a reservoir attached or included in a device may contain IMPIα or IMPIα-fusions actively or passively deployed so that the device is situated in an area with known high load of target bacteria.

EXAMPLES

1. Measurements of Extracellular DNA in Microtitre Tray Cultures

A method for tracking eDNA (extracellular DNA) was derived and compiled partly from similar procedures and conditions found in the literature and modified by the inventors.

The reference strain *P. aeruginosa* (DSM No. 50071; MIC 8 mg/liter), partially resistant to Gentamycin, was studied in parallel with a clinical isolate of *P. aeruginosa* PAO1 (DSM No. 19880) to evaluate eDNA accumulation over time in the presence and absence of IMPI. First the strains were cultured in NB medium (Nutrient Broth No. 4) overnight at 37° C. and grown to stationary phase. From these bacteria, 5 µl were used to inoculate 96-well black flat bottom plates (Greiner) containing NB medium (200 µl). The NB medium contained either double concentrated NB medium (2×; 100 µl) diluted with 100 µl TBS-buffer (Negative Control) or medium diluted with IMPI, which was previously solved in TBS (100 µl; Positive Control). The final concentration of IMPI per well was 35 µM for experiments with *P. aeruginosa* DSM 50071 and DSM 19880 respectively. To stain extracellular DNA and membrane-compromised (dead) bacteria in aggregates of *P. aeruginosa*, 1 µL of 1 mm stock solution of BOBO-3 stain (Life Technologies) was added to 5 mL cultures at the start of growth experiments (incubation in the dark). BOBO-3 is a membrane-impermeable fluorescent dye (Aex570, em602) that binds to DNA and therefore specifically stains extracellular DNA which Images were taken over 48 h by a high-definition area scan (99×99 points) on a well of a 96-well microplate using a synergy H4 plate reader (Biotek).

2. MIC Determination and OD-Measurement

Gentamycin MIC (minimal inhibitory concentration) values were determined using a standard two fold microtiter broth dilution protocol with Nutrient Broth as medium. Midexponential phase cultures of *P. aeruginosa* reference strain DSM No.: 50071 and two antibiotic-resistant clinical isolates (*P. aeruginosa* VB7623 and VB7444), which were isolated from the tracheal secrete of a patient, were tested. Antimicrobial susceptibility testing of the clinical isolates was performed by the University Clinic Tubingen. Typically gentamicin concentrations between 8 µg/ml and 0.0625 µg/ml were chosen to estimated bacterial growth and determine the MIC values. Further, the OD (optical density) at 600 nm in the presence and absence of the insect metalloprotease inhibitor IMPI was investigated. For assessing influences of IMPI on bacterial growth final concentrations of IMPI between 20 and 75 µM were used. Bacterial growth was monitored at 37° C. over 48 h. All MIC values were done as triplicates.

The subsequent table lists the sequences printed in the ensuing sequence protocol. The leading number denotes the SEQ ID NO for the nucleotide sequence, the subsequent even number missing number would denote the SEQ ID NO of the respective peptide sequence.

1 IMPIalpha (wild type or wtIMPIalpha)
  3 IMPIbeta (wild type or wt IMPIbeta)
  5 GST/IMPIalpha
  7 GST/IMPIbeta
  9: IMPIalpha Pos37 NnG Pos38 InL Pos39 RnA
 11: GST/IMPIalpha Pos37 NnG Pos38 InL Pos39 RnA
 13: IMPIalpha Pos52 RnK
 15: GST/IMPIalpha Pos52 RnK
 17: IMPI Pos35 InL
 19: IMPI Pos35 InM 21: IMPI Pos35 InF
23: IMPI Pos35 InC
25: IMPI Pos35 InN
27: IMPI Pos35 InQ
29: IMPI Pos35 InH
31: IMPI Pos35 InK
33: IMPI Pos35 InR
35: IMPI Pos36 InV
37: IMPI Pos36 InM
39: IMPI Pos36 InF
41: IMPI Pos36 InW
43: IMPI Pos36 InY
45: IMPI Pos36 InS
47: IMPI Pos36 InT
49: IMPI Pos36 InN
51: IMPI Pos36 InQ
53: IMPI Pos36 InH
55: IMPI Pos36 InR
57: IMPI Pos36 InK
59: IMPI Pos39 InV
61: IMPI Pos39 InK
63: IMPI Pos35 InW
65: IMPI Pos35 InY
67: IMPI Pos39 RnA
69: IMPI Pos35 InC
71: IMPI Pos35 InK
73: IMPI Pos35 InR
75: IMPI Pos35 InL
77: IMPI Pos35 InM
79: IMPI Pos35 InF
81: IMPI Pos35 InQ
83: IMPI Pos35 InH
85: GST/IMPI Pos35 InN
87: GST/IMPI Pos36 InS
89: GST/IMPI Pos39 InK
91: GST/IMPI Pos35 InC
93: IMPI signal peptide,
95: IMPI like (*Solenopsis*, Peptide only, no nucleotide sequence provided)

REFERENCES

Aloush, V., et al., Multidrug-resistant *Pseudomonas aeruginosa*: risk factors and clinical impact. Antimicrob Agents Chemother, 2006. 50(1): p. 43-8.

Cathcart G. R., Greer B., Harriott P., Lynas J. F., Gilmore B. F., Walker B. "Novel Inhibitors of the *Pseudomonas aeruginosa* Virulence Factor LasB: a Potential Therapeutic Approach for the Attenuation of Virulence Mechanisms in Pseudomonal Infection" Antimicrob Agents Chemother. 2011 June; 55(6):2670-8

Chung M., Popova T. G., Millis B. A., Mukherjee D. V., Zhou W., Liotta L. A., Petricoin E. F., Chandhoke V., Bailey Ch., Popov S. G., "Secreted Neutral Metalloproteases of *Bacillus anthracis* as Candidate Pathogenic Factors" JBC 281, 42, (2006) 31408-31418, DOI 10.1074/jbc. M605526200

Khan M. T. H., Fuskevaag O. M. and Sylte I. Discovery of Potent Thermolysin Inhibitors Using Structure Based Virtual Screening and Binding Assays. *Journal of Medicinal Chemistry* 52 (2009) 48-61

Lebrun, I., et al., Bacterial toxins: an overview on bacterial proteases and their action as virulence factors. Mini Rev Med Chem, 2009. 9(7): p. 820-8

Milla, C. E., et al., Anti-PcrV antibody in cystic fibrosis: A novel approach targeting *Pseudomonas aeruginosa* airway infection. Pediatr Pulmonol, 2013

Popov S. G., Popova T. G., Hopkins S., Weinstein R. S., MacAfee R., Fryxell K. J., Chandhoke V., Bailey Ch., Alibek K. "Effective antiprotease-antibiotic treatment of experiment Sivanmaliappan, T. S. and M. Sevanan, Antimicrobial Susceptibility Patterns of *Pseudomonas aeruginosa* from Diabetes Patients with Foot Ulcers. Int J Microbiol, 2011. 2011: p. 605195

Schmidtchen A., Hoist E., Tapper H., Bjorck, L. Elastase-producing *Pseudomonas aeruginosa* degrade plasma proteins and extracellular products of human skin and fibroblasts, and inhibit fibroblast growth Microb. Pathog. 34 (2003) 47-55

Smith A. W., Chahal B., French G. L. The human gastric pathogen *Helicobacter pylori* has a gene encoding an enzyme first classified as a mucinase in *Vibrio cholerae* Mol. Microbiol. 13 (1994) 153-160

El Solh, A. A. and A. Alhajhusain, Update on the treatment of *Pseudomonas* aeruginosa pneumonia. The Journal of antimicrobial chemotherapy, 2009. 64(2): p. 229-38.

Strateva, T. and D. Yordanov, *Pseudomonas aeruginosa*—a phenomenon of bacterial resistance. Journal of medical microbiology, 2009. 58(Pt 9): p. 1133-48.

Wedde M, Weise C, Kopacek P, Franke P, Vilcinskas A. Purification and characterization of an inducible metalloprotease inhibitor from the hemolymph of greater wax moth larvae, *Galleria mellonella*. Eur 3 Biochem 1998; 255:534-43

Zimlichman, E., et al., "Health Care-Associated Infections: A Meta-analysis of Costs and Financial Impact on the US Health Care System." JAMA Intern Med, 2013.

What is claimed is:

1. A composition comprising: a polypeptide comprising at least 80% sequence identity to SEQ ID NO. 2, wherein the polypeptide is selected from the group consisting of IMPIα, an IMPIα-fusion, and both an IMPIα and an IMPIα-fusion; and at least one antibiotic compound, wherein the at least one antibiotic compound comprises an aminoglycoside antibiotic, further wherein the polypeptide and the at least one antibiotic compound are in concentrations which exhibit in combination a synergistic effect against resistant bacteria.

2. The composition of claim 1, wherein the polypeptide is selected from the group consisting of SEQ ID NOs: 10, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, and IMPIα-fusions, having amino acid sequences selected from the group consisting of SEQ ID NOs: 6, 8, 12, 86, 88, 90, and 92.

3. A composition of claim 1, wherein the IMPIα polypeptide has at least 90% sequence identity to SEQ ID No: 2, representing the wild-type of the protein insect metalloproteinase inhibitor IMPIα.

4. A method of treating or preventing a bacterial infection in a subject, the method comprising administering the composition of claim 1 to a subject suffering from or at risk of suffering from a bacterial infection.

5. The method of claim 4, wherein the at least one antibiotic compound:
   (i) is administered in doses lower than inhibitory upon solitary application, or in higher doses up to maximally tolerable doses, and
   (ii) is administered essentially simultaneous with IMPIα or separately in an individual dosing scheme, frequency, and treatment duration.

6. A pharmaceutical composition comprising the composition of claim 1, and a carrier suitable for injection, inhalation or topical application.

7. A method of sterilizing a device comprising coating the device with the composition of claim 1.

8. The method of claim 7, wherein the device is an implant.

9. The composition of claim 1, wherein the polypeptide is SEQ ID NO. 2.

10. The composition of claim 1, wherein the IMPIα concentration is at 20 µM.

11. The composition of claim 1, wherein the IMPIα concentration is at 45 µM.

12. The composition of claim 1, wherein the polypeptide is the IMPIα-fusion.

13. The composition of claim 1, further comprising a bactericidal compound.

* * * * *